(12) United States Patent
Shetty et al.

(10) Patent No.: US 8,697,840 B2
(45) Date of Patent: Apr. 15, 2014

(54) PEPTIDE INHIBITION OF LUNG EPITHELIAL APOPTOSIS AND PULMONARY FIBROSIS

(75) Inventors: Sreerama Shetty, Tyler, TX (US); Steven Idell, Tyler, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 559 days.

(21) Appl. No.: 12/398,757

(22) Filed: Mar. 5, 2009

(65) Prior Publication Data

US 2009/0227515 A1 Sep. 10, 2009

Related U.S. Application Data

(60) Provisional application No. 61/033,999, filed on Mar. 5, 2008.

(51) Int. Cl.
*C07K 11/00* (2006.01)

(52) U.S. Cl.
USPC ........... 530/326; 530/327; 530/328; 530/329; 530/330; 514/21.4; 514/21.5

(58) Field of Classification Search
USPC ......... 530/326, 327, 328, 329; 514/21.4, 21.5
See application file for complete search history.

(56) References Cited

U.S. PATENT DOCUMENTS

| | | | | |
|---|---|---|---|---|
| 4,021,387 A | * | 5/1977 | Goetzl et al. | 525/54.11 |
| 4,628,045 A | * | 12/1986 | Hahn | 530/330 |
| 4,816,449 A | * | 3/1989 | Hahn | 514/12.2 |
| 5,728,680 A | * | 3/1998 | Morozov et al. | 514/13.5 |
| 6,126,939 A | * | 10/2000 | Eisenbach-Schwartz et al. | 424/185.1 |
| 2003/0165510 A1 | | 9/2003 | Sessa | |

OTHER PUBLICATIONS

Le Saux, C.J. et al., The Journal of Biological Chemistry 283(9): 5760-5768 (2008).
Levin, A.M.. et al., ACS Chemical Biology 2(7): 493-500 (2007).
Odajima, N. et al., Journal of Histochemistry & Cytochemistry 55(9): 899-909 (2007).
Tourkina, E. et al., Am J Physiol Lung Cell Mol Physiol 294:L843-L861 (2008).

* cited by examiner

*Primary Examiner* — David Lukton
(74) *Attorney, Agent, or Firm* — Browdy and Neimark, PLLC

(57) ABSTRACT

During lung injury, p53 expression increases, inducing plasminogen activator inhibitor-1 (PAI-1) while inhibiting expression of urokinase-type plasminogen activator (uPA) and its receptor (uPAR), resulting in apoptosis of lung epithelial cells (LECs). In the bleomycin lung injury model, p53 and PAI-1 are induced while uPA and uPAR are inhibited. A 20 residue peptide DGIWKASFTTFTVTKYWFYR termed PP-1 (the Cav-1 scaffolding domain) or peptide NYHYL-ESSMTALYTLGH, termed PP-2, protected LECs from bleomycin-induced apoptosis in vitro and in vivo and prevented subsequent pulmonary fibrosis by attenuating lung epitheilial damage. Pharmaceutical compositions, peptide multimers and deliverable polypeptides comprising the above peptides are dislcosed. The peptides and functional variants, peptide multimers, cell-targeted polyepeptides and pharmaceutical compositions are used in methods for inhibiting apoptosis of injured or damaged lung epithelial cells and for treating acute lung injury and consequent pulmonary fibrosis.

14 Claims, 14 Drawing Sheets

FIG. 9

PEPTIDE INHIBITION OF LUNG EPITHELIAL APOPTOSIS AND PULMONARY FIBROSIS

This application claims priority to provisional application 61/033,999, filed Mar. 5, 2008.

STATEMENT OF RIGHTS TO INVENTIONS MADE UNDER FEDERALLY SPONSORED RESEARCH

This invention was funded in part by a grant from the National Heart, Lung and Blood Institute, National Institutes of Health (R01-HL71147), which provides to the United States government certain rights in this invention.

BACKGROUND OF THE INVENTION

1. Field of the Invention

The present invention in the field of biochemistry and medicine is directed to peptides designated PP-1 and PP-2, and functional variants thereof, that prevent apoptosis of lung epithelial cells in vitro and in vivo, and prevent or treat pulmonary fibrosis, making them useful for treating acute lung inflammation and its sequelae, primarily pulmonary fibrosis.

2. Description of the Background Art

Throughout the disclosure, references are cited either by a number(s) in parentheses, referring to the Documents list at the end, or by insertion of the cite into the text.

Expression of urokinase plasminogen activator (uPA) the uPA receptor (uPAR), plasminogen activator inhibitor-1 (PAI-1) and p53 by lung epithelial cells ("LEC") independently influence a broad range of processes implicated in the pathogenesis of acute lung injury ("ALI") and its repair (1-5). These processes include cellular proteolysis, adhesion, migration (6), and cellular viability (5).

The present inventors and colleagues recently described extensive cross-talk between the uPA/uPAR/PAI-1 system, p53, and the viability of LECs (5, 7-9). They discovered that uPA-mediated signaling regulates expression of p53 by LECs, which in turn regulates uPA and uPAR or reciprocally promotes expression of the pro-apoptotic effector; PAI-1 (10-12). While these interactions comprise a new paradigm, their role in the pathogenesis of lung injury and pulmonary fibrosis is not yet fully elucidated. This deficiency in the prior art is addressed in part by the present invention.

Lung expression of uPA, uPAR and PAI-1 is of particular importance in the control of proteolysis, fibroblast viability and lung remodeling in Acute Respiratory Distress Syndrome (ARDS) and other forms of ALI (13-20), and interstitial lung diseases (6,13-29). uPA is mitogenic for several cell lines as well as LECs (5, 30-39). The present inventors' group (2-4) and others (40-42) recently showed that uPA regulates PA activity of LECs by inducing its own expression as well as uPAR and PAI-1. These responses occurred as a result of stabilization of the respective mRNAs (2-4). Further studies showed that uPA also regulates epithelial cell apoptosis/survival through regulation of p53 (5) which controls reciprocal expression of uPA (12), its receptor uPAR (10) and its major inhibitor PAI-1 (11) at the posttranscriptional level and involves a novel cell surface signaling interaction between uPA, uPAR, caveolin-1 ("Cav-1") and β1-integrin (5). Based on the appreciation of the foregoing, the present inventors conceived of new compositions and methods for treating ALI and its consequent remodeling reactions.

uPA and PAI-1 Expression by LECs.

Plasminogen present in plasma or extravascular fluids can be converted to the active endopeptidase plasmin by uPA or tissue-type PA (tPA) (1, 32). While tPA is mainly responsible for intravascular thrombolysis, uPA is involved in extravascular proteolysis and tissue remodeling (47). Two endogenous PA inhibitors, PAI-1 and PAI-2, are produced in epithelial cells, endothelial cells and platelets and (1,4,32,46-51). PAI-1 is primarily responsible for the fibrinolytic defect in bronchoalveolar lavage (BAL) fluids of ARDS patients (6, 13-23). In concert with other resident lung cells, LECs contribute to the derangements seen in these fluids. uPAR and uPA allow proximate activation of plasminogen at the surface of the lung epithelium. This proteolytic system operates in the setting of lung injury and remodeling. The discoveries of the present inventors shed new light on the pathogenesis of both processes (7,15, 19).

uPAR (Vassalli et al., *J. Cell. Biol.*, 100:86, 1985; Ploug et al, *J. Biol. Chem.*, 273:13933, 1998) is a highly glycosylated, glycosyl-phosphoinositol (GPI)-linked receptor implicated in uPA-mediated cellular signaling (2, 52), adhesion (6), proteolysis, differentiation (1, 32, 53) and proliferation (5, 30-33). uPAR also congregates at the leading edge of migrating cells, facilitating cell movement (53-54). uPAR has three extracellular domains (D1-D3) and binds uPA with high affinity via its receptor-binding domain, D1 in the N-terminal portion of the molecule. The functions of D2 and D3 have not been completely elucidated. uPAR binds active 54 kDa uPA, not the low molecular weight (33 kDa) form of active u-PA (Vassalli et al., supra; Cubeilis et al., *J. Biol. Chem.*, 261: 15819-22, 1986). Binding to the receptor does not require the catalytic site of uPA and the binding determinant is in the N-terminal part of the enzyme which (in the primary structure) is remote from the catalytic site. The receptor binding domain is in the 15 kDa N terminal fragment ("ATF", residues 1-135) uPA, more precisely within the Cys-rich region, termed the growth factor region due to homology to the receptor-binding part of epidermal growth factor (EGF). Amino acid residues 12-32 of uPA appear to be critical for binding (Appella et al., *J. Biol. Chem.*, 262:4437-40, 1987).

LECs synthesize and secrete a 55 kDa proenzyme, the single chain form of uPA (or scuPA), which is activated by plasmin and other proteases. LECs also synthesize and express uPAR. LECs express PAI-1 (4,50,55-56), which inhibits uPA activity and promotes cycling of tripartite uPA/uPAR/PAI-1 complexes from the cell surface. Expression of uPA, uPAR and PAI-1 in these cells is augmented by proinflammatory stimuli or inhaled particulates (57-58). Understanding the regulatory interactions of these molecules is currently limited. The discoveries disclosed herein describe new pathways by which these molecules are regulated at the level of mRNA stability. See FIG. 1.

Derangements of Fibrinolysis in Pathogenesis of Human ALI and Pulmonary Fibrosis Extravascular fibrin promotes the inflammatory response and fibrotic repair after injury (15,18-19). Plasmin facilitates remodeling of the fibrin neomatrix (19). Plasmin generates peptides that injure endothelial cells and induce microvascular leakage (59-60). Plasmin degrades extracellular matrix (ECM) proteins such as laminin and fibronectin and facilitates destruction of collagen and elastin by activating latent matrix metalloproteinases. Thus, successful repair of injured lung parenchyma requires precise balance of plasmin activity.

A deficiency of alveolar plasmin activity characterizes acute and chronic lung injuries. Human BAL fluid normally exhibits high levels of uPA activity, but uPA-dependent fibrinolytic activity is reduced in patients with idiopathic pulmonary fibrosis (IPF), sarcoidosis, ARDS, or severe pneumonias (14-16, 17, 19, 21-23). This defect is mainly attributable to local overexpression of PAI-1 (13-15,28-29). In ALI, uPA is primarily complexed with PAI-1, which is internalized in complex with uPAR and is relatively unavailable to affect local proteolysis or otherwise participate in normal LEC signaling interactions. These conditions perpetuate florid extravascular fibrin in ARDS and other types of lung injury (14-26). Collectively, these observations implicate uPA, uPAR and PAI-1 in the pathogenesis and repair of acute lung injury.

p53 and the Fibrinolytic System in Fibrotic Repair after ALI

Bleomycin ("bleo"), a potent chemotherapeutic agent, causes fibrotic lung disease in humans, rats and mice (25-27, 43-45,61-66) and induces acute lung injury before the onset of fibrosis (67-70). Bleo's cytotoxic effect is believed to involve binding to and cleaving DNA (70-74) as a necessary step in development of pulmonary fibrosis (71-72). Bleomycin-induced DNA damage in the lung leads to increased intrapulmonary expression of p53 (69). Cells with elevated p53 typically arrest in the G1 phase and either undergo DNA repair or apoptosis. Increased bleo-induced lung injury occurs with suppression of p53 (75). Complete deficiency of p53 would be deleterious, permitting the persistence of severely damaged LECs and other damaged lung resident cells.

Intratracheal instillation of bleo likewise augments alveolar expression of PAI-1 (25-27,61-64) and p53 (69) and studies of transgenic animals also support a critical role for uPA and its inhibition by PAI-1 in the pathogenesis of pulmonary fibrosis (26-27). PAI-1 deficiency, exogenous uPA and induction of lung-specific uPA protect mice from bleo-induced lung injury (62-64).

Based on these observations, the present inventors conceived that interactions between uPA, p53 and other key components of the fibrinolytic system critically influence outcomes in lung inflammation and repair, and conceived of the therapeutic peptides described herein.

LEC Apoptosis in the Pathogenesis of Lung Inflammation and Pulmonary Fibrosis:

Lung diseases such as ARDS, IPF and other interstitial lung diseases are characterized by LEC apoptosis and progressive fibrosis (18). In asthma and chronic obstructive pulmonary disease (COPD), fibrotic changes occur with apoptosis of the airway epithelium and within subepithelial tissues of the conducting airways (28-29). In all these diseases, remodeling of the lung matrix and LEC apoptosis appear to be mechanistically linked (13,18). Recent reviews suggest a close relationship between uPA-uPAR-mediated matrix remodeling, cellular viability and LEC proliferation (18,76). However, up until the present invention, there was a paucity of evidence directly linking the coordinate control of LEC viability to interactions of uPA with p53.

The present inventors' group recently found that uPA regulates LEC apoptosis and proliferation through elaboration of p53 in a bi-phasic, dose-dependent manner (5).

uPA interacts with uPAR to promote local proteolysis as well as cell proliferation and migration (1-2,5,31,53-54), which are implicated in the pathogenesis of lung inflammation and remodeling. The present inventors' group found that uPA enhanced uPA protein and mRNA expression in human Beas2B cells and primary human small airway LECs (3). The induction was mediated through uPAR. uPA-induced uPA expression involved stabilization of uPA mRNA. Autoinduction of uPA by exposure of LECs to uPA is a newly defined pathway by which this protease can influence expression of local fibrinolytic activity and other uPA-dependent cellular signaling responses germane to lung inflammation (77).

The present inventors' group also found that uPA enhanced uPAR expression and $^{125}$I-uPA binding in Beas2B and primary human small airway LECs (2). Induction of uPAR by uPA likewise involved uPAR mRNA stabilization (30). This induction represents a novel pathway by which LECs regulate uPAR-dependent cellular responses that contribute to remodeling in lung injury. Induction of both uPA and uPAR by uPA was blocked by a tyrosine kinase inhibitor and potentiated by prevention of dephosphorylation (2-3,30).

Most recently, the present inventors' group found that uPA enhanced PAI-1 protein and mRNA expression in Beas2B and human LECs. Similar to induction of uPA or uPAR expression, uPA-mediated induction of PAI-1 involved post-transcriptional stabilization of PAI-1 mRNA. Induction of PAI-1 by exposure of LECs to uPA is a newly recognized pathway by which PAI-1 could regulate local fibrinolysis and uPA-dependent cellular responses in the setting of lung injury. The regulation of PAI-1, uPA and uPAR by uPA exposure to LECs represents a newly recognized regulatory mechanism that operates at the level of message stability.

p53 Regulates Expression of uPA, uPAR and PAI-1

The present inventors noted that p53 regulated uPA expression by direct interaction with uPA mRNA. Inhibition of p53 expression by RNA silencing enhanced basal and uPA-mediated uPA protein and mRNA expression with mRNA stabilization. Purified p53 bound to a 35 nucleotide uPA mRNA 3'UTR in a sequence-specific manner, which confirmed a new role for p53 as a uPA mRNA binding protein that reduces its stability and thereby reduces cellular uPA expression (12). The present inventors and colleagues recently reported that p53$^{-/-}$ (H1299) cells expressed robust levels of cell surface uPAR and uPAR mRNA (10). Expression of p53 protein in p53$^{-/-}$ cells suppressed basal and uPA-induced cell surface uPAR protein and increased uPAR mRNA degradation. uPA protein and mRNA were decreased in p53 deficient cells, and introduction of wild-type p53 increased PAI-1 protein and mRNA levels.

These observations demonstrated a novel role for p53 as an mRNA binding protein that increased PAI-1 while decreasing uPAR and uPA expression in human LECs, demonstrating a novel forward feedback system in which p53 regulates expression of key components of the fibrinolytic system by direct binding to specific sequences of the uPA, uPAR and PAI-1 3'UTR, respectively. The present inventors conceived of an important role for these interactions in the regulation of the apoptosis or viability of LECs disclosed herein.

β1-Integrin Signaling in uPA Induction of uPA and uPAR with Concurrent Suppression of PAI-1 and p53: Protection against LEC Apoptosis The present inventors' group recently showed that pretreatment of cells with anti-β1-integrin antibody blocked uPA-induced p53 expression (5). β1-integrin is associated with uPAR at the LEC surface (78-79), and Cav-1 co-precipitates with uPAR/β1-integrin complexes indicating cross-interaction (80-81). Description of Cav-1, and its scaffolding domain (CSD) are described below.

Anti-β1-integrin antibody activated β1-integrin in LECs by clustering of signaling intermediates, mimicking the effects of relatively high-concentrations (>10 nM) of uPA. Put another way, uPA concentrations >10 nM and activation of cell surface β1-integrin stimulated uPA and uPAR expression while blocking expression of PAI-1 and p53: the net result is protection of LECs from apoptosis. These uPA concentrations are consistent with those used therapeutically (82-

88) and may be present in plasma or extravascular fluids in pathophysiologic conditions including sepsis or pneumonia (89).

The present inventors and colleagues found that uPA-mediated Stat3 tyrosine (Y705) phosphorylation (activation) is mediated by interaction of uPA with uPAR (31). uPA also increased uPAR association with β-integrin (89-90) and EGF receptor (EGFR), and directly bound to GP130 in LECs (91). GP130 and EGFR are both receptors that induce Stat3 activation (92-93).

A variety of cells may be stimulated to express uPA during ALI or its resolution, and uPAR and/or other receptors could localize relatively high concentrations of uPA at the cell surface during ALI resolution. The present inventors have conceived that during early ALI, uPA is largely bound by excess PAI-1, undergoing inactivation and accelerated recycling (36, 46). As uPA has blocks bleo-induced fibrosis when delivered by aerosol (94), the effects of 20 nM uPA on LECs are likewise relevant in an interventional context.

Caveolin-1 ("Cav-1") and the Caveolin-1 Scaffolding Domain (CSD)

Caveolin-1, a 22 kDa integral membrane protein, is a principal structural and regulatory component of cell membrane caveolae. Li, S. et al., 1996, *J Biol Chem.* 271:29182-90, described biological activities of caveolin and the fragment CSD of residues 82-101 corresponding to the cytosolic domain. Caveolin interacted with wild-type c-Src but did not form a stable complex with mutationally activated v-Src. The Src-interacting domain of Cav-1 was within residues 82-101. The CSD functionally suppressed the auto-activation of purified recombinant c-Src tyrosine kinase. This CSD had the following features: (1) was required to form multivalent homo-oligomers of caveolin (2) interacted with G-protein α-subunits and down-regulated their GTPase activity. (3) bound to wild-type H-Ras.(4) it is membrane-proximal, suggesting that it may be involved in other potential protein-protein interactions.

Toya Y et al., *Endocrinology,* 1998, 139:2025-31, showed that CSD inhibited cardiac adenylyl cyclase more potently than tissue adenylyl cyclases, and suggested use of the peptide as an isoform-selective adenylyl cyclase inhibitor.

Engelman J A et al., *J Biol Chem.,* 1998, 273:20448-55, found that caveolins may function as negative regulators of signal transduction because mutational activation of the c-Neu oncogene down-regulated Cav-1 protein expression in certain cultured cells, and conversely, recombinant overexpression of Cav-1 blocked Neu-mediated signal transduction in vivo. The CSD peptide was sufficient to inhibit Neu autophosphorylation.

Ghosh S et al., *J Biol Chem.,* 1998, 273:22267-71 disclosed that endothelial nitric-oxide synthase (eNOS) is targeted to caveoli through interaction with Cav-1 and that the CSD peptide equivalently inhibited NO synthesis and NADPH oxidation by full-length eNOS. The authors proposed that Cav-1 binding to the eNOS reductase domain compromises its ability to bind calmodulin (CaM) and donate electrons to the eNOS heme, thereby inhibiting NO synthesis.

Yamamoto M et al., *Exp Cell Res.* 1999, 247:380-8, disclosed that platelet-derived growth factor (PDGF) receptors interacted with Cav-1 in fibroblasts and showed that the CSD peptide from Cav-1 (and from caveolin-3, but not caveolin-2), inhibited PDGF-R autophosphorylation. Cav-1 directly bound to PDGF receptors.

Carman C V et al., *J Biol Chem.* 1999 274:8858-64, studied regulation of G protein-coupled receptor kinases (GRK's) by caveolin and discovered a specific interaction of GRK2 with the CSD.

Kim J H et al., *Biochemistry.* 1999, 38:3763-9, reported that Cav-1 interacts with phospholipase D1 (PLD1) via the CSD.

Schlegel, A. et al., *J Biol Chem.,* 1999, 274:22660-7, showed that the CSD was necessary and sufficient for Cav-1-mediated membrane binding in vitro leading to the conclusion that CSD contributes to the membrane attachment of Cav-1.

Nystrom F H et al., *Mol Endocrinol.* 1999 13:2013-24, disclosed that the CSD binds to a Cav-1 binding motif in the insulin receptor (InsR) kinase domain in vitro. which may differentially modulate insulin signaling to enhance insulin action in cells in which (heterologous) InsRs were expressed but to inhibit insulin effects in fat cells.

Schlegel A et al., *J Biol Chem.,* 2000, 275:21605-17, reported that two separate regions of the Cav-1, one of which was CSD, could anchor green fluorescent protein (GFP) to membranes in vivo. CSD targeted GFP to caveolae, albeit less efficiently than full-length Cav-1

Bucci, M, et al., *Nature Med.,* 2000, 6:1362-7, discloses that Cav-1 regulates signal transduction through binding of the CSD to key signaling molecules. However, it was noted that the physiological importance of Cav-1 in regulating signaling has been difficult to distinguish from its traditional functions in caveolar assembly, transcytosis, and cholesterol transport. A chimeric peptide with a cellular internalization sequence fused to the CSD was efficiently taken up into blood vessels and endothelial cells, and selectively inhibited acetylcholine (Ach)-induced vasodilation and NO production. Systemic administration of the fusion peptide suppressed acute inflammation and vascular leak in mice to the same extent as did a glucocorticoid or an eNOS inhibitor.

Zhu L et al., *Am J Physiol Heart Circ Physiol.,* 2004 286:H195-201, disclosed that facilitated internalization of the CSD attenuated an increase in microvessel permeability mediated platelet-activating factor. Je H D et al., *Am J Physiol Heart Circ Physiol.* 2004, 286:H91-8, utilized a decoy peptide approach to define the involvement of Cav-1 in PKC-dependent regulation of vascular smooth muscle contractility and found that it has a role in coordinating signaling leading to the regulation of contractility Gaudreault S B et al., *J Biol Chem.* 2004, 279:356-62, stated that Cav-1 inhibits the activity of most of its interacting partners. A CSD peptide dramatically inhibited cPLA2 synaptoneurosomes and abolished activation of endogenous PLA2 activity with KCl or melittin. This inhibitory action disclosed as being specific (because a scrambled version of this peptide had no effect). The authors concluded that Cav-1, may interfere with synaptic facilitation and long term potentiation formation in the hippocampus.

Li L et al., *Mol Cell Biol.,* 2003, 23:9389-9404 disclosed that Cav-1 maintains activated Akt in prostate cancer cells through interactions of the CSD with binding sites on serine/threonine protein phosphatases which are inhibited.

Sato Y et al., *J Biol Chem.* 2004, 279:8827-36, examined the molecular mechanism for inhibition of NO formation by Cav-1 studying the CSD peptide and found that Cav-1 inhibits nNos by a different mechanism than for eNOS and (2) the CSD peptide inhibits interdomain electron transfer from the reductase domain to the oxygenase domain.

Williams T M et al., *J Biol Chem.* 2004, 279:51630-46, stated that Cav-1 influences the development of human cancers, studying Cav-1 in mammary tumorigenesis and lung metastasis. Complete loss of Cav-1 was required to accelerate tumorigenesis and metastasis. Recombinant expression of Cav-1 in a highly metastatic variant line caused an almost 5-fold reduction in invasion in vitro along with marked reductions in MMP-9 and MMP-2 secretion and enzymatic activity and diminished ERK-½ signaling in response to growth factor stimulation. Delivery of a cell permeable peptide encoding the CSD into Met-1 cells was sufficient to inhibit invasion.

Le Lan C et al., *FEBS Lett.* 2006 580:5301-5, analyzed the conformational properties of two synthetic peptides, D82-R101 and D82-I109 (both encompassing the CSD (D82-R101)) and reported that a stable helical conformation of the CSD in a membrane mimicking system was only present when the peptide included the L102-I109 hydrophobic stretch, a part of the caveolin intra-membrane domain.

Song L et al., *Blood.* 2007, 109:1515-23 discussed reduced expression of Cav-1 accompanying the diminished expression of tight junction (TJ)-associated proteins following stimulation of brain microvascular endothelial cells (BMECs) with the chemokine CCL2.

Huang J H et al., *J Biol Chem.* 2007, 282:6143-52, identified a positive clone in a 12-mer phage peptide library displaying a peptide sequence with high binding to the HIV-1 gp41 core. Cav-1 was said to be a known gp41-binding protein; the 12mer sequence contained a putative gp41-binding motif which also exists in the CSD. The authors suggested this interaction may be essential for fusion pore formation or viral endocytosis and could thereby affect pathogenesis.

Levin A M et al., *ACS Chem Biol.* 2007, 2:493-500, using double barrel shotgun scanning to dissect binding to two or more targets through combinatorial mutagenesis of one protein that binds to multiple targets, found that the CSD bound to and inhibited both eNOS and protein kinase A (PKA). The CSD oligomerized and deoligomerized to modulate its binding affinity to partner proteins.

In a publication appearing after the making of the present invention, Tourkina E et al., *Am J Physiol Lung Cell Mol Physiol.* 294:L843-61 (2008 May) (Epub Jan. 18, 2008) stated that lung fibrosis involves overexpression of ECM proteins, primarily collagen, by α-smooth muscle actin (ASMA)-positive cells. Cav-1 was described as a master regulator of collagen expression by cultured lung fibroblasts and of lung fibrosis in vivo. A peptide equivalent to the CSD inhibited collagen and tenascin-C expression by normal lung fibroblasts (NLF) and fibroblasts from scleroderma patients' fibrotic lungs (SLF). CSD peptide inhibited ASMA expression in SLF, but not in NLF. Upregulation of Cav-1 expression by adenovirus resulted in similar inhibition of collagen, tenascin-C, and ASMA expression. The authors suggested that low Cav-1 levels in SLF caused overexpression of collagen, tenascin-C, and ASMA. MEK, ERK, Jun N-terminal kinase, and Akt were hyperactivated in SLF; CSD peptide inhibited their activation and altered their subcellular localization. The paper also disclosed that alterations in signaling molecule activation observed in SLF also occurred in fibrotic lung tissue of scleroderma patients and in mice with bleo-induced lung fibrosis. Systemic administration of CSD peptide to bleo-treated mice blocked epithelial cell apoptosis, inflammatory cell infiltration, changes in tissue morphology, signaling molecule activation and collagen, tenascin-C, and ASMA expression associated with lung fibrosis. The authors stated that "CSD peptide may be a prototype treatment for human lung fibrosis that acts in part by inhibiting expression of ASMA and ECM proteins."

SUMMARY OF THE INVENTION

Induction of uPA and uPAR by LECs represent survival/proliferation signals whereas p53 and PAI-1 expression conversely signal apoptotic responses by these cells. The underlying mechanisms are discussed below. These observations suggested that the control of LEC viability is regulated via the coordinate regulation of uPA-induced signaling of components of the fibrinolytic system and p53. Published and preliminary results by the present inventors provide the first direct link between regulation of LEC survival and the fibrinolytic system.

According to the present invention, this pathway is a cardinal determinant of epithelial cell apoptosis and subsequent fibrotic repair associated with ALI.

The present inventors have discovered that treatment with either of two peptides, PP-1 and PP-2 (sequences provided below), that are believed to act by inhibition of uPAR-Cav-1 interactions and PAR-β1-integrin associated Src kinase activity, protect LECs from bleo-induced apoptosis. This is believed to be mediated by suppression of the proapototic molecules p53 and PAI-1 while enhancing the expression of pro-survival (or anti-apoptotic) molecules uPA and uPAR.

These peptides similarly block bleo-induced mouse lung fibrosis by attenuating lung epithelial damage. While not wishing to be bound to a particular mechanism, it is believed that the mechanism of this effect involves competitive inhibition of uPAR-β1-integrin mediated activation of Src kinase which leads to suppression of p53 and p53-mediated PAI-1 expression as well as increased LEC production of uPA and uPAR which rescues the LECs from apoptotic cell death. The present invention includes compositions that comprise or consist of these peptides, described in more detail below, as well as methods of their use.

The peptides that have been found to act in the manner described above are:

(1) Protective Peptide-1 or PP-1 the amino acid sequence of which is DGIWKASFTTFTVTKYWFYR (SEQ ID NO:1). This peptide corresponds to residues 82-101 of caveolin-1 (CSD). In some of the Figures provided herein, this PP-1 is referred to as "PP".

(2) Protective peptide-2 or PP-2 which consists of the amino acid sequence NYHYLESSMTALYTLGH (SEQ ID NO:3).

The present invention includes the first demonstration that PP-1 and PP-2 inhibit LEC death. The present invention provides novel methods to inhibit or reduce LEC apoptosis, and, thereby, acute lung inflammatory injury and the consequent pulmonary fibrosis that occurs as a result of repair mechanisms using PP-1, PP-2 or biologically active functional variants thereof, including substitution variants, addition variants, deletion variants, peptide multimers, fusion polypeptides (including with cell-delivery moieties) and peptidomimetics thereof. These are described in detail in the sections that follow.

The invention is also directed to an anti-apoptotic pharmaceutical composition comprising an effective amount of the peptide or variant or multimer, etc., described above and a pharmaceutically acceptable carrier. Preferably, the therapeutic composition is in a form suitable for injection or for lung instillation.

Also provided is a method for inhibiting apoptosis, comprising contacting LECs (or other cells the apoptosis of which are similarly inhibited) with an effective amount of the peptide or variant described above, or with a pharmaceutical composition as above, in vivo.

Also provided is a method for inhibiting apoptosis of cells, preferably of LECs, in a subject in need of such inhibition, comprising administering to the subject an effective amount of the above peptide or variant, preferably in the form of the pharmaceutical composition.

The invention is also directed to a method for treating a subject having a disease or condition characterized by acute lung injury or pulmonary fibrosis that is associated with apoptosis of lung epithelium, comprising administering to the subject an effective amount of a pharmaceutical composition as described above.

Finally, one embodiment is directed to the use of the above peptide, variant, multimer, fusion peptide, etc., for the manufacture of a medicament for use in inhibiting apoptosis of injured or damaged lung epithelial cells in a subject in need thereof, or for use in treating a subject having a disease or condition characterized by acute lung injury or pulmonary fibrosis that is associated with apoptosis of lung epithelial apoptosis.

BRIEF DESCRIPTION OF THE DRAWINGS

FIG. 1B. In the normal lung or lung undergoing recovering from injury, more uPA is locally available at the surface of LECs, as less is complexed to saturating increments in PAI-1 (that occur in ALI). Less uPA is recycled through internalization of uPA/PAI-1/uPAR complexes. These relatively increased levels of uPA preferentially bind LECs via low affinity receptors (including GP130 or EGFR), which signal for Mdm2 via Stat3 tyrosine phosphorylation. Mdm2 in turn suppresses p53 though ubiquitination. The paucity of p53 in LECs under these conditions prevents binding of p53 to uPA and uPAR mRNA, so that these transcripts remain stable. uPA and uPAR levels in LECs are preserved and serve as survival signals. PAI-1 levels are reciprocally suppressed as p53 concurrently fails to bind PAI-1 mRNA. The latter transcripts remain unstable under these conditions so that PAI-1 levels remain low. The relative increment of uPA and uPAR vs. PAI-1 protects against apoptosis of LECs.

FIG. 2A, SAE cells were treated for 48 h with 0-20 nM uPA at 37° C. Apoptotic cells were analyzed by flow cytometry using anti-annexin-V antibody and propidium iodide (PI). Bleo (40 μg/ml) was used as positive control (90). FIG. 2B, The cells were next treated with uPA as described in FIG. 1A and DNA synthesis was determined by [$^3$H]-thymidine uptake as described (5).

FIG. 9 is a set of photomicrographs showing that PP-1 treatment prevented bleomycin-induced lung epithelial cell degradation of poly (ADP-ribose) polymerase (PARP). Mice were injected i.p. with PP-1 (4.5 μM) or control peptide (CP-1) on days 1 and 2. On day 2 mice were treated with bleomycin (40 μg/50μl) by intranasal instillation. Mice were sacrificed 24, 48 and 72 h after later, lungs were excised, inflated and fixed in formalin, and 5 μM sections were analyzed by immunohistochemistry (IHC) using an antibody specific for cleaved PARP.

FIG. 10A shows hydroxyproline levels, a measure of collagen deposition, and FIG. 10B shows desmosine levels, a measure of elastin, in lungs of mice treated with saline or 50 μg Bleo intranasally. 24 h after bleo, 0.1 ml osmotic pump filled with 10 mM PP-1 (designated "Bleo+PP" in Figures) or CP1 control scrambled peptide ("Bleo+CP1") were implanted intraperitoneally. Lungs were harvested after 21 days, homogenized and the homogenates were subjected to the analysis of hydroxyproline or desmosine levels.

DESCRIPTION OF THE PREFERRED EMBODIMENTS

Figures 1A, 1B:
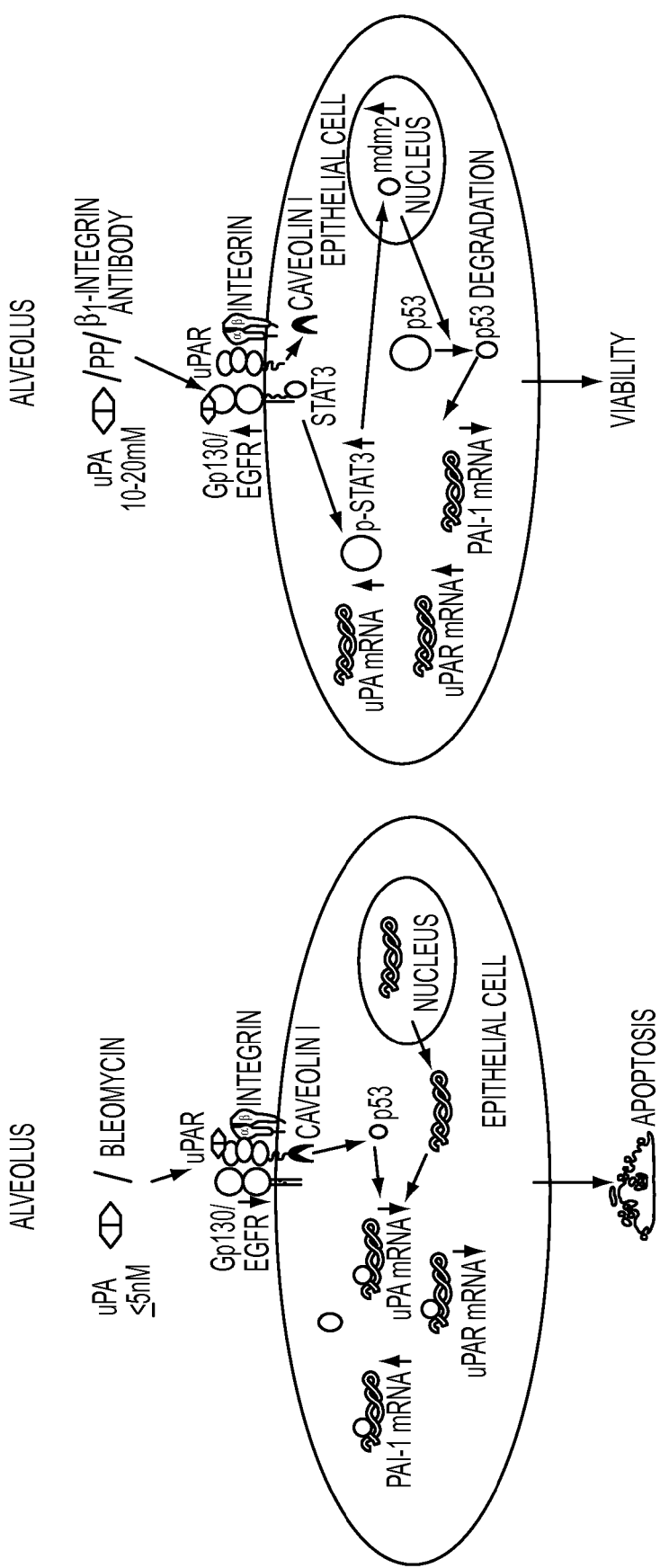
FIGS. 1A and 1B is a schematic illustration showing the postulated links between p53-mediated regulation of the fibrinolytic system and control of LEC viability. This illustration shows, based on published information and some of the inventors' present findings, a new paradigm by which the fibrinolytic system and p53 interface to regulate LEC apoptosis vs. viability. As shown in the left panel (FIG. 1A), ALI induces p53 via DNA damage in LECs. p53 binds to uPA, uPAR and PAI-1 transcripts, resulting in reciprocal suppression of uPA and uPAR, with an increment in PAI-1. Mediators released during injury (TNF-α, TGF-β among others) induce uPA which is available at relatively low levels (0.5-2 nM) because of inhibition by PAI-1 (and other serpins). uPA levels are kept relatively low at the LEC surface through inhibitor complex formation and their internalization by LECs (35,46). Signaling by uPA under these conditions preferentially occurs via uPAR, uPA's high affinity receptor. These conditions inhibit Stat3 tyrosine (Y705) phosphorylation and induce PAI-1 expression through p53-mediated stabilization of PAI-1 transcripts, leading to apoptosis.

During lung injury, tumor suppressor protein p53 expression is increased which in turn induces PAI-1 while inhibiting expression of uPA and its receptor uPAR. Induction of PAI-1 and/or inhibition of uPA and uPAR causes epithelial cells to die. Lung injury caused by bleomycin (Bleo) induces p53 and PAI-1 while inhibiting uPA and uPAR expression. Induction of p53 involves signals transduced through β1-integrin-uPAR complex. Recent reports (5, 10-12) and new results from the present inventors support the central hypothesis that coordinate changes of p53 and p53-mediated changes in uPA, uPAR and PAI-1 in LECs protect the lung epithelium and mitigate lung fibrosis after ALI. This hypothesis is strongly supported by several lines of evidence developed by the present inventors' group and others.

The Cav-1 scaffolding domain peptide which interferes with caveolin-1 interaction with Src kinases mimics the combined effect of uPA and anti-β1-integrin antibody as discussed in more detail below. Native human Cav-1 has a length of 178 amino acids and a molecular weight of 22 kDa. The amino acid sequence of Cav-1 is shown below (SEQ ID NO:5).

Two preferred peptides of the present invention affect how p53 regulates LEC viability via coordinate control of uPA, uPAR (up) and PAI-1 expression (down) and by this presumed mechanism, protect LECs or lung epithelium in vivo from apoptosis and block fibrosis that results from ALI.

(1) Protective Peptide-1 or PP-1 consists of the amino acid sequence DGIWKASFTTFTVTKYWFYR (SEQ ID NO:1). This peptide corresponds to residues 82-101 of human Cav-1 which constitute the scaffolding domain of this protein (sometimes abbreviated CSD). (In some of the Figures provided herein, the PP-1 peptide is referred to as "PP"). In studies disclosed herein, a control peptide for PP-1, which is termed CP-1 is a scrambled peptide with the same amino acid composition, but a different sequence. The sequence of CP-1 is WGIDKAFFTTSTVTYKWFRY (SEQ ID NO:2).

(2) Protective peptid-2 or PP-2 consists of the amino acid sequence NYHYLESSMTALYTLGH (SEQ ID NO:3). This peptide is not known to exist in nature and was initially disclosed as a control, scrambled, peptide sequence for the peptide AESTYHHLSLGYMYTLN (SEQ ID NO:4) by Wei Y et al., 1996, *Science* 273: 1551-55). The latter peptide (referred to as Peptide 25 in that publication, but which is termed CP-2 here because it is utilized as a control for PP-2) was discovered during a screen of a phage library for peptides that bound uPAR but did not interfere with the binding of uPAR to vitronectin or uPA. As shown in that publication, Peptide 25, but not its control (which is PP-2 here) inhibited uPAR-dependent adhesion of cells to vitronectin. Peptide 25, but not its control, disrupted integrin-caveolin-uPAR complexes at a concentration that blocked adhesion. uPAR-mediated adhesion to vitronectin correlated with the formation of multimeric membrane complexes of integrins, caveolin, and uPAR itself. Hence, the uPAR-integrin-caveolin complex was concluded to represent a functional unit that mediates uPAR-dependent cell adhesion and modifies integrin function.

The human Cav-1 protein from which the PP-1 fragment is derived is a 178 amino acid protein (SEQ ID NO:5) shown below. The residues making up the CSD scaffolding domain (SEQ ID NO:1, is underscored:

For example, a PP-1 or PP-2 variant may be generated, preferably synthetically but also by recombinant production, and tested for the binding properties or activity of PP-1 or PP-2 to identify those residues and positions that are important for such activity. A preferred way to measure the activity of the variant is in a competitive binding assay wherein the ability of the peptide variant to compete with binding of soluble caveolin, such as one that is detectably labeled, with soluble uPAR ("suPAR").

In terms of functional variants or equivalents, those skilled in the art appreciate that for maintenance of the requisite biochemical or biological function, there is a limit to the number and nature of substitutions or other changes that can be made in the peptide and still yield a molecule with an acceptable level of equivalent biological or biochemical activity. The functional variants of the present invention are thus defined herein as those peptides or polypeptides in which certain, though not most or all, of the amino acids are substituted.

It is understood that distinct peptide variants of PP-1 or PP-2, and longer polypeptides comprising (a) PP-1 (b) a PP-1 variant, (c) PP-2 or (d) a PP-2 variant, may easily be made in accordance with the invention, either by chemical (synthetic) methods or by recombinant means (preferred for longer polypeptides).

Amino Acid Substitution and Addition Variants

PP-1 and PP-2 substitution variants of the present invention preferably have no more than five conservative substitutions, preferably no more than four, preferably no more than three, preferably nor more than two and more preferably no

```
  1 MSGGKYVDSE GHLYTVPIRE QGNIYKPNNK AMADELSEKQ VYDAHTKEID LVNRDPKHLN

61 DDVVKIDFED VIAEPEGTHS FDGIWKASFT TFTVTKYWFY RLLSALFGIP MALIWGIYFA

121 ILSFLHIWAV VPCIKSFLIE IQCISRVYSI YVHTVCDPLF EAVGKIFSNV RINLQKEI
```

Functional Variants, Peptidomimetics and Rational Drug Design

Modifications and changes may be made in the structure of the PP-1 or PP-2 peptide molecules of the present invention, and to create molecules with similar or otherwise desirable characteristics. Such functional variants or biologically active variants (which terms are used interchangeably) are encompassed within the present invention.

A preferred functional variant of PP-1 or PP-2 is an amino acid substitution variant that retains the biological and biochemical activity of the parent PP-1 or PP-2 peptide.

Also included here are deletion variants, addition variants, as well as fusion constructs, peptide oligomers/multimers, etc.

It is well-known that certain amino acids may be substituted for others in a peptide or polypeptide without appreciable loss of biochemical activity such as binding to ligands. Examples are antigen-binding regions of antibodies, binding sites on substrate molecules or receptors, etc. Since when a peptide or polypeptide functions by in interacting with another molecule, such as another protein, polypeptide or peptide, such an interaction defines the molecule's biological functional activity. It is well known that certain amino acid substitutions can be made in proteinaceous molecules while retaining the relevant interactive, e.g., binding properties.

It is thus contemplated that various changes may be made in the sequence of PP-1 or PP-2 peptides or polypeptides comprising PP-1 or PP-2 without appreciable loss of their biological activity or their utility in accordance with this invention.

more than one substituted amino acid residue, For a detailed description of protein chemistry and structure, see Schulz, G E et al., *Principles of Protein Structure*, Springer-Verlag, New York, 1979, and Creighton, T E, *Proteins: Structure and Molecular Principles*, W.H. Freeman & Co., San Francisco, 1984, which are hereby incorporated by reference. The preferred types of substitutions are conservative substitutions which are well-known in the art and are set forth below in an exemplary manner defined as exchanges within one of the following groups:

1. Small aliphatic, nonpolar or slightly polar residues: e.g., Ala, Ser, Thr, Gly;
2. Polar, negatively charged residues and their amides: e.g., Asp, Asn, Glu, Gln;
3. Polar, positively charged residues: e.g., His, Arg, Lys;
4. Larger aromatic residues, e.g., Phe, Trp, Tyr Pro, because of its unusual geometry, tightly constrains the chain. More substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Most substitutions according to the present invention are those that do not produce marked diminution in the functional characteristics of the peptide molecule. Even when it is difficult to predict the exact effect of a substitution in advance, one skilled in the art will appreciate that the effect can be evaluated by routine screening assays, preferably the binding assay discussed above or the biological assays (e.g., inhibition of apoptosis as exemplified herein). Modifications of peptide properties including redox or thermal stability, hydrophobicity, susceptibility to proteolytic degradation or the tendency to aggregate with carriers or into multimers are tested by methods well known to those of skill in the art. It will be appreciated that that loss of stability, increase in tendency to aggregate, increased susceptibility to proteolysis, etc., are to be avoided.

Included in within the definition of functional variants of PP-1 or PP-2 are addition which preferably comprise an additional 1-5 amino acids at either terminus or at both termini. In other embodiments (which are intended to be distinct from the peptide multimers discussed below), further additional residues may be added, as long as the polypeptide does not exceed a total length of about 100 residues, The additional residues may be added not only to SEQ ID NO:1 or SEQ ID NO:3 but also to variants thereof, such as to conservative substitution variants.

In preferred addition variants of PP-1, the additional residues are those found natively in Cav-1 (SEQ ID NO:5, N-terminal to, and/or C-terminal to SEQ ID NO:1 (the core PP-1 peptide). Alternatively, other amino acids can be added at either terminus, with the understanding that the addition variant maintains the biological activity and binding activity of PP-1 (at least 20% of the activity, or greater, as is set forth below). Addition variants of PP-2 are subject to the same length preferences and limitations, and can include any residues the addition of which preserve the biological activity of the core peptide, preferably at least 20% of the activity.

It is understood that in a case in which one or more residues are shown to be particularly important to the biological function or structural integrity of a peptide or polypeptide herein, such as residues in a binding region, such residues generally are not to be varied. In this manner, functional variants defined herein as those peptides which maintain a substantial amount of the biochemical or biological activity of the native or reference peptide can be identified.

Consideration of an amino acid's hydropathic index permits achievement of more quantitative changes. Each amino acid has been assigned a hydropathic index on the basis of its hydrophobicity and charge characteristics, as follows:: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). The importance of the hydropathic amino acid index in conferring interactive biological function on a peptide or polypeptide molecule is generally understood in the art (see, for example, Kyte and Doolittle, 1982). Again, it is known that certain amino acids may be substituted for other amino acids having a similar hydropathic index or score and still retain a similar biological activity. In substituting based on the hydropathic index, it is preferred to use substituting residues with hydropathic indices within ±2, more preferably within ±1, and even more preferably to substitute with a hydropathic index within ±0.5. It is also known in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); Asp (+3.0±1); Glu (+3.0±1); Ser (+0.3); Asn (+0.2); Gln (+0.2); Gly (0); Thr (−0.4); Pro (−0.5±1); Ala (−0.5); His (−0.5); Cys (−1.0); Met(−1.3); Val (−1.5); Leu (−1.8); isoleucine (−1.8); Tyr (−2.3); Phe (−2.5); Trp (−3.4).

In substituting residues based upon similar hydrophilicity values, the substitution of amino acids whose hydrophilicity values are within ±2 is preferred, those within ±1 are more preferred, and those within ±0.5 are even more preferred.

In addition to the 20 "standard" L-amino acids, modified or unusual amino acids which are well-defined in the art are also contemplated for use in the present invention.

Other compounds may be designed by rational drug design to function in manner similar to PP-1 or PP-2. The goal of rational drug design is to produce structural analogs of biologically active compounds. By creating such analogs, it is possible to produce drugs that are more active or more stable than the natural molecules (i.e., peptides), lower susceptibility to alterations which affect functions. One approach is to generate a three-dimensional structure of PP-1 or PP-2, for example, by NMR or X-ray crystallography, computer modeling or by a combination. An alternative approach is to replace randomly functional groups in the PP-1 or PP-2 sequence, and determine the affect on function.

In examining amino acid substitution variants of PP-1 or PP-2, the variants preferably have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of amino acids that are identical to, or that are conservative substitutions of, the amino acids of SEQ ID NO:1 or of SEQ ID NO:3, provided the biological activity of the peptide is maintained.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at the URL gcg.com), using either a Blossom 62 matrix or a PAM250 matrix, and a gap weight of 16, 14, 12, 10, 8, 6, or 4 and a length weight of 1, 2, 3, 4, 5, or 6.

In another embodiment, the percent identity between two amino acid sequences is determined using the algorithm of E. Meyers et al. (CABIOS, 4:11-17 (1989)) which has been incorporated into the ALIGN program (version 2.0), using a PAM120 weight residue table, a gap length penalty of 12 and a gap penalty of 4.

The amino acid sequences of the present invention can further be used as a "query sequence" to perform a search against public databases, for example, to identify other family members or related sequences. Such searches can be performed using the XBLAST programs (version 2.0) of Altschul et al. (1990) *J. Mol. Biol.* 215:403-10. BLAST searches can be performed with the XBLAST program, score=50, wordlength=3 to obtain amino acid sequences homologous to the native PP-1 sequence or to the PP-2 sequence. To obtain gapped alignments for comparison purposes, Gapped BLAST can be utilized as described in Altschul et al. (1997) *Nucl Acids Res.* 25:3389-3402. When utilizing BLAST and Gapped BLAST programs, the default parameters of XBLAST can be used. See the website having the URL "ncbi.nlm.nih.gov."

A preferred composition is, or comprises, a biologically active variant or derivative of PP-1 or PP-2 characterized in that it possesses the binding activity and/or biological activity of PP-1 or PP-2. Such binding is to a ligand (or "receptor") that is preferably soluble uPAR or cell surface uPAR which binding can be assessed in conventional receptor-binding assays using whole cells, membrane preparations thereof, or purified receptor molecules.

Moreover, a biologically active variant has the activity of PP-1 or PP-2 in an in vitro or in vivo assay of binding or of biological activity, such as assays described herein. Preferably the polypeptide inhibits or prevents apoptosis of LECs induced by bleo in vitro or in vivo with activity at least about 20% of the activity of PP-1 or PP-2, preferably at least 30%, more preferably at least 40%, more preferably at least 50%, more preferably at least 60%, more preferably at least 70%, more preferably at least 80%, more preferably at least 90%, more preferably at least 95%. The variant may have 100% or even greater activity than PP-1 or PP-2.

The peptide may be capped at its N and C termini with an acyl (abbreviated "Ac")-and an amido (abbreviated "Am") group, respectively, for example acetyl ($CH_3CO$—) at the N terminus and amido (—$NH_2$) at the C terminus. A broad range of N-terminal capping functions, preferably in a linkage to the terminal amino group, is contemplated, for example: formyl;

alkanoyl, having from 1 to 10 carbon atoms, such as acetyl, propionyl, butyryl;

alkenoyl, having from 1 to 10 carbon atoms, such as hex-3-enoyl;

alkynoyl, having from 1 to 10 carbon atoms, such as hex-5-ynoyl;

aroyl, such as benzoyl or 1-naphthoyl;

heteroaroyl, such as 3-pyrroyl or 4-quinoloyl;

alkylsulfonyl, such as methanesulfonyl;

arylsulfonyl, such as benzenesulfonyl or sulfanilyl;

heteroarylsulfonyl, such as pyridine-4-sulfonyl;

substituted alkanoyl, having from 1 to 10 carbon atoms, such as 4-aminobutyryl;

substituted alkenoyl, having from 1 to 10 carbon atoms, such as 6-hydroxy-hex-3-enoyl;

substituted alkynoyl, having from 1 to 10 carbon atoms, such as 3-hydroxy-hex-5-ynoyl;

substituted aroyl, such as 4-chlorobenzoyl or 8-hydroxy-naphth-2-oyl;

substituted heteroaroyl, such as 2,4-dioxo-1,2,3,4-tetrahydro-3-methyl-quinazolin-6-oyl;

substituted alkylsulfonyl, such as 2-aminoethanesulfonyl;

substituted arylsulfonyl, such as 5-dimethylamino-1-naphthalenesulfonyl;

substituted heteroarylsulfonyl, such as 1-methoxy-6-isoquinolinesulfonyl;

carbamoyl or thiocarbamoyl;

substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl;

substituted carbamoyl (R'—NH—CO) and substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined.

The C-terminal capping function can either be in an amide or ester bond with the terminal carboxyl. Capping functions that provide for an amide bond are designated as $NR^1R^2$ wherein $R^1$ and $R^2$ may be independently drawn from the following group: hydrogen;

alkyl, preferably having from 1 to 10 carbon atoms, such as methyl, ethyl, isopropyl;

alkenyl, preferably having from 1 to 10 carbon atoms, such as prop-2-enyl;

alkynyl, preferably having from 1 to 10 carbon atoms, such as prop-2-ynyl;

substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl;

substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl;

substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl;

aroylalkyl having up to 10 carbon atoms, such as phenacyl or 2-benzoylethyl;

aryl, such as phenyl or 1-naphthyl;

heteroaryl, such as 4-quinolyl;

alkanoyl having from 1 to 10 carbon atoms, such as acetyl or butyryl;

aroyl, such as benzoyl;

heteroaroyl, such as 3-quinoloyl;

OR' or NR'R" where R' and R" are independently hydrogen, alkyl, aryl, heteroaryl, acyl, aroyl, sulfonyl, sulfinyl, or $SO_2$—R''' or SO—R''' where R''' is substituted or unsubstituted alkyl, aryl, heteroaryl, alkenyl, or alkynyl.

Capping functions that provide for an ester bond are designated as OR, wherein R may be: alkoxy; aryloxy; heteroaryloxy; aralkyloxy; heteroaralkyloxy; substituted alkoxy; substituted aryloxy; substituted heteroaryloxy; substituted aralkyloxy; or substituted heteroaralkyloxy.

Either the N-terminal or the C-terminal capping function, or both, may be of such structure that the capped molecule functions as a prodrug (a pharmacologically inactive derivative of the parent drug molecule) that undergoes spontaneous or enzymatic transformation within the body in order to release the active drug and that has improved delivery properties over the parent drug molecule (Bundgaard H, Ed: *Design of Prodrugs*, Elsevier, Amsterdam, 1985).

Judicious choice of capping groups allows the addition of other activities on the peptide. For example, the presence of a sulfhydryl group linked to the N- or C-terminal cap will permit conjugation of the derivatized peptide to other molecules.

Production of Peptides, Polypeptides and Derivatives
General Chemical Synthetic Procedures Polypeptides comprising the sequence of PP-1 or PP-2, or a functional variant sequence thereof, may be prepared using recombinant DNA technology. Basic texts disclosing general methods of molecular biology, all of which are incorporated by reference, include: Sambrook, J. et al., *Molecular Cloning: A Laboratory Manual*, 2nd Edition, Cold Spring Harbor Press, Cold Spring Harbor, N.Y., 1989; Ausubel, F M et al. *Current Protocols in Molecular Biology*, Vol. 2, Wiley-Interscience, New York, (current edition); Kriegler, *Gene Transfer and Expression: A Laboratory Manual* (1990); Glover, D M, ed, *DNA Cloning: A Practical Approach*, vol. I & II, IRL Press, 1985; Albers, B. et al., *Molecular Biology of the Cell*, 2nd Ed., Garland Publishing, Inc., New York, N.Y. (1989); Watson, J D et al., *Recombinant DNA*, 2nd Ed., Scientific American Books, New York, 1992; and Old, R W et al.,

*Principles of Gene Manipulation: An Introduction to Genetic Engineering*, 2nd Ed., University of California Press, Berkeley, Calif. (1981).

Shorter polypeptides or peptides, e.g., between about 15 and about 40 amino acids in length are preferably prepared using solid-phase synthesis such as that generally described by Merrifield, *J. Amer. Chem. Soc.*, 85:2149-54 (1963), although other equivalent chemical syntheses known in the art are also useful. Solid-phase peptide synthesis may be initiated from the C-terminus of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA resin or MBHA resin. Such methods, well-known in the art, are disclosed, for example, in U.S. Pat. No. 5,994,309 which is incorporated by reference in its entirety.

Multimeric or Oligomeric Peptides

The present invention also includes longer peptides built from repeating units of one or more sequences of PP-1, PP-2, or a functional variant or biologically active variant thereof that has the anti-apoptotic and protective activity of PP-1 and PP-2. The preferred peptide unit of such a multimer is DGI-WKASFTTFTVTKYWFYR (SEQ ID NO:1) or NYHYL-ESSMTALYTLGH (SEQ ID NO:3). Addition variants of these peptides that may be the "unit" of the multimer preferably include from 1-4 additional amino acids.

Such multimers may be built from any of the foregoing two peptides or their variants as described herein. Moreover, a peptide multimer may comprise different combinations of peptide monomers (which may include either or both of SEQ ID NO:1 and SEQ ID NO:3 or variants thereof. Such oligomeric or multimeric peptides can be made by chemical synthesis or by recombinant DNA techniques as discussed herein. When produced by chemical synthesis, the oligomers preferably have from 2-5 repeats of a core peptide sequence, and the total number of amino acids in the multimer should not exceed about 160 residues, preferably not more than 100 residues (or their equivalents, when including linkers or spacers).

A preferred synthetic chemical peptide multimer has the formula $$P^1_n$$

wherein the core peptide $P^1$ is SEQ ID NO:1 or 3 or a substitution variant thereof, and wherein n=2–5, and wherein the core peptide alone or in oligo- or multimeric form has the biological activity of PP-1 and PP-2 as disclosed herein in an in vitro or in vivo bioassay of such activity.

In another embodiment, a preferred synthetic chemical peptide multimer has the formula $$(P^1\text{-}X_m)_n\text{-}P^2$$

$P^1$ and $P^2$ are the core peptides described above, including functional variants, wherein
(a) $P^1$ and $P^2$ may be the same or different; moreover, each occurrence of $P^1$ in the multimer may be a different peptide (or variant);
(b) X is a spacer which comprises or consists of:
  (i) a short organic chain, preferably $C_1$-$C_5$ alkyl, $C_1$-$C_5$ alkenyl, $C_1$-$C_5$ alkynyl, $C_1$-$C_5$ polyether containing up to 4 oxygen atoms, wherein m=0 or 1 and n=1-7; or
  (ii) $Gly_z$ wherein, z=1-6,
  and wherein the core peptide alone or in multimeric form has the biological activity of PP-1 and PP-2 as disclosed herein in an in vitro or in vivo assay of such activity.

When produced recombinantly, a preferred spacer is $Gly_z$ as described above, where z=1-6, and the multimers may have as many repeats of the core peptide sequence as the expression system permits, for example from two to about 25 repeats. A preferred recombinantly produced peptide multimer has the formula:

$$(P^1\text{-}Gly_z)_n\text{-}P^2$$

wherein:
(a) $P^1$ and $P^2$ are, independently, SEQ ID NO:1 or 3 or a substitution or addition variant thereof, wherein $P^1$ and $P^2$ may be the same or different; moreover, each occurrence of $P^1$ in the multimer may be a different peptide (or variant); wherein
n=1-25 and z=0-6; (preferred ranges of n include n=1-5, 1-10, 1-15, or 1-20) and wherein the core peptide alone or in multimeric form has the biological activity of PP-1 and PP-2 as disclosed herein in an in vitro or in vivo bioassay of such activity.

In the present peptide multimers, either $P^1$ or $P^2$ is preferably SEQ ID NO:1 or SEQ ID NO:3 or a conservative substitution variant thereof. The multimer is optionally capped. It is understood that such multimers may be built from any of the peptides or variants described herein. It is also understood that the peptide multimer should be different from SEQ ID NO:5 (i.e., not native human Cav-1 and is preferably not a native mammalian Cav-1 homologue).

Chemical Derivatives of PP-1 or PP-2

In addition to the capping groups described above, "chemical derivatives" of PP-1 or PP-2 contain additional chemical moieties not normally a part of a protein or peptide. Covalent modifications of the polypeptide are included within the scope of this invention. Such derivatized moieties may improve the solubility, absorption, biological half life, and the like. Moieties capable of mediating such effects are disclosed, for example, Gennaro, A R, *Remington: The Science and Practice of Pharmacy*, Lippincott Williams & Wilkins Publishers; 21st Ed, 2005 (or latest edition)

Such modifications may be introduced into the molecule by reacting targeted amino acid residues of the polypeptide with an organic derivatizing agent that is capable of reacting with selected side chains or terminal residues. Another modification is cyclization of the protein.

Cysteinyl residues most commonly are reacted with α-haloacetates (and corresponding amines) to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate (pH 5.5-7.0) which agent is relatively specific for the histidyl side chain. p-bromophenacyl bromide also is useful; the reaction is preferably performed in 0.1 M sodium cacodylate at pH 6.0.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4pentanedione; and transaminase-catalyzed reaction with glyoxylate.

Arginyl residues are modified by reaction with one or several conventional reagents, including phenylglyoxal, 2,3-butanedione, 1,2-cyclohexanedione, and ninhydrin. Such derivatization requires that the reaction be performed in alkaline conditions because of the high $pK_a$ of the guanidine functional group. Furthermore, these reagents may react with the groups of lysine as well as the arginine ϵ-amino group.

Modification of tyrosyl residues has permits introduction of spectral labels into a polypeptide. This is accomplished by reaction with aromatic diazonium compounds or tetranitromethane. Most commonly, N-acetylimidizol and tetranitromethane are used to create O-acetyl tyrosyl species and 3-nitro derivatives, respectively.

Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonia.

Aspartyl and glutamyl residues are converted to asparaginyl and glutaminyl residues by reaction with ammonium ions. Conversely, glutaminyl and asparaginyl residues may be deamidated to the corresponding glutamyl and aspartyl residues. Deamidation can be performed under mildly acidic conditions.

Derivatization with bifunctional agents is useful for cross-linking the polypeptide to a water-insoluble support matrix or other macromolecular carrier. Commonly used cross-linking agents include 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of the hydroxyl groups of seryl or threonyl residues, methylation of the α-amino groups of lysine, arginine, and histidine side chains (Creighton, supra), acetylation of the N-terminal amine, and, in some instances, amidation of the C-terminal carboxyl groups. Also included are polypeptides wherein one or more D-amino acids are substituted for one or more L-amino acids.

Peptidomimetics

Also included within the scope of this invention is a peptidomimetic compound which mimics the biological effects of PP-1 or PP-2. A peptidomimetic agent may be an unnatural peptide or a non-peptide agent that recreates the stereospatial properties of the binding elements of PP-1 or PP-2 such that it has the binding activity and biological activity of PP-1 or PP-2. Similar to a biologically active PP-1 or PP-2 peptide, peptide multimer or polypeptide, a peptidomimetic will have a binding face (which interacts with any ligand to which PP-1 or PP-2 binds) and a non-binding face. Again, similar to PP-1 or PP-2, the non-binding face of a peptidomimetic will contain functional groups which can be modified by coupling various therapeutic moieties without modifying the binding face of the peptidomimetic. A preferred embodiment of a peptidomimetic would contain an aniline on the non-binding face of the molecule. The $NH_2$-group of an aniline has a pKa ~4.5 and could therefore be modified by any $NH_2$-selective reagent without modifying any $NH_2$ functional groups on the binding face of the peptidomimetic. Other peptidomimetics may not have any $NH_2$ functional groups on their binding face and therefore, any $NH_2$, without regard for $pK_a$ could be displayed on the non-binding face as a site for conjugation. In addition other modifiable functional groups, such as —SH and —COOH could be incorporated into the non-binding face of a peptidomimetic as a site of conjugation. A therapeutic moiety could also be directly incorporated during the synthesis of a peptidomimetic and preferentially be displayed on the non-binding face of the molecule.

This invention also includes compounds that retain partial peptide characteristics. For example, any proteolytically unstable bond within a peptide of the invention could be selectively replaced by a non-peptidic element such as an isostere (N-methylation; D-amino acid) or a reduced peptide bond while the rest of the molecule retains its peptidic nature.

Peptidomimetic compounds, either agonists, substrates or inhibitors, have been described for a number of bioactive peptides/polypeptides such as opioid peptides, VIP, thrombin, HIV protease, etc. Methods for designing and preparing peptidomimetic compounds are known in the art (Hruby, V J, *Biopolymers* 33:1073-1082 (1993); Wiley, R A et al., *Med. Res. Rev.* 13:327-384 (1993); Moore et al., *Adv. in Pharmacol* 33:91-141 (1995); Giannis et al., *Adv. in Drug Res.* 29:1-78 (1997). Certain mimetics that mimic secondary structure are described in Johnson et al., In: *Biotechnology and Pharmacy*, Pezzuto et al., Chapman and Hall (Eds.), NY, 1993. These methods are used to make peptidomimetics that possess at least the binding capacity and specificity of the PP-1 or PP-2 polypeptides and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the three-dimensional structure of a peptide of the invention either free or bound in complex with a ligand (e.g., soluble uPAR or a fragment thereof). Alternatively, the structure of a peptide of the invention bound to its ligand can be gained by the techniques of nuclear magnetic resonance spectroscopy. Greater knowledge of the stereochemistry of the interaction of the peptide with its ligand or receptor will permit the rational design of such peptidomimetic agents. The structure of a peptide or polypeptide of the invention in the absence of ligand could also provide a scaffold for the design of mimetic molecules.

Deliverable Peptides/Polypeptides

One embodiment of the invention comprises a method of introducing the peptide of the invention into animal cells, such as human cells. Compositions useful for this method, referred to as "deliverable" or "cell-deliverable" or "cell-targeted" peptides or polypeptides comprise a biologically active peptide according to the invention, such as PP-1 or PP-2, or a functional variant thereof, or a peptide multimer thereof, that has attached thereto or is associated with, a further component which serves as an "internalization sequence" or cellular delivery system. The term "associated with" may include chemically bonded or coupled to, whether by covalent or other bonds or forces, or combined with, as in a mixture. As used herein, "delivery" refers to internalizing a peptide/polypeptide in a cell, Delivery molecules contemplated herein include polypeptides or peptides used by others to effect cellular entry. See for example, Morris et al., *Nature Biotechnology*, 19:1173-6, 2001). A preferred strategy is as follows: an apoptosis-inhibiting ("biologically active") peptide or polypeptide of the invention is bonded to or mixed with a specially designed peptide which facilitates its entry into cells, preferably human cells. This delivery system does not require the delivery peptide to be fused or chemically coupled to biologically active peptide or polypeptide (although that is preferred), nor does biologically active peptide or polypeptide have to be denatured prior to the delivery or internalization process. A disadvantage of earlier delivery systems is the requirement for denaturation of the "payload" protein prior to delivery and subsequent intracellular renaturation. These embodiments are based on known approaches for promoting protein translocation into cells.

One type of "delivery" peptide/polypeptide which promotes translocation/internalization includes the HIV-TAT protein (Frankel, A D et al., Cell 55:1189-93 (1998), and the third α helix from the Antennapedia homeodomain (Derossi et al., J. Biol. Chem. 269:10444-50 (1994); Lindgren, M et al., Trends Pharm. Sci. 21:99-103 (2000). The latter peptide, also known as "penetratin" is a 16-amino acid peptide with the wild-type sequence RQIKIWFQNRRMKWKK (SEQ ID NO:6) or two analogues/variants designated W48F (RQIKIFFQNRRMKWKK, SEQ ID NO:7) and W56F (RQIKIWFQNRRMKFKK, SEQ ID NO:8) (Christiaens B et al., Eur J Biochem 2002, 269:2918-2926). Another variant with both of the above mutations is RQIKIFFQNRRMKFKK (SEQ ID NO:9).

Another protein (family) includes VP22, a herpes simplex virus protein that has the remarkable property of intercellular transport and distributes a protein to many surrounding cells (Elliott, G et al., 1997, Cell 88:223-33; O'Hare et al., U.S. Pat. 6,017,735). For example, VP22 linked to p53 (Phelan, A. et al., 1998, Nat Biotechnol 16:440-3) or thymidine kinase (Dilber, M S et al., 1999, Gene Ther 6:12-21) facilitating the spread of linked proteins to surrounding cells in vitro. Also useful are VP22 homologues in other herpes viruses, such as the avian Marek's Disease Virus (MDV) protein UL49, that shares homology with HSV-1 VP22 (Koptidesova et al., 1995, Arch Virol. 140:355-62) and has been shown to be capable of intercellular transport after exogenous application (Dorange et al., 2000, J Gen Virol. 81:2219). All these proteins share the property of intercellular spread that provide an approach for enhancing cellular uptake of the peptides, variants, and multimers of this invention.

Also included are "functional derivatives" of the above intercellular spreading or "delivery" or "internalization" proteins and peptides such as HIV-TAT or VP22 which include homologous amino acid substitution variants, fragments or chemical derivatives, which terms are herein for the biologically active peptides. A functional derivative retains measurable translocation or intercellular spreading (VP22-like) activity that promotes entry of the desired polypeptide, which promotes the utility of the present biologically active peptide e.g., for therapy. "Functional derivatives" encompass variants (preferably conservative substitution variants) and fragments regardless of whether the terms are used in the conjunctive or the alternative.

Because the above transport proteins are said to work best when conjugated or otherwise bound to the peptide or polypeptide they are transporting, such as PP-1 or PP-2, there are a number of disadvantages when using them. A more effective delivery polypeptide that can be admixed with the biologically active peptide and does not need to be chemically bonded for its action is described in Morris et al., supra, as "Pep-1" (but referred to herein as "DelPep-1" to avoid confusion with PP-1) which has the amphipathic amino acid sequence KETWWETWWTEWSQPKKKRKV (SEQ ID NO:10). DelPep-1 consists of three domains:

(1) a hydrophobic Trp-rich motif containing five Trp residues KETWWETWWTEW (residues 1-12 of SEQ ID NO:10 above). This motif is desirable, or required, for efficient targeting to cell membrane and for entering into hydrophobic interactions with proteins;

(2) a hydrophilic Lys-rich domain KKKRKV (the 6 C-terminal residues of SEQ ID NO:10) which is derived from the nuclear localization sequence of SV40 virus large T antigen, and improves intracellular delivery and peptide solubility; and (3) a spacer "domain" SQP (3 internal residues of SEQ ID NO:10) which and separate the two active domains above and include a Pro that improves flexibility and integrity of both the hydrophobic and hydrophilic domains.

Accordingly, another embodiment of the invention is a deliverable peptide or polypeptide comprising PP-1, PP-2, or a functional variant thereof as described above, and a delivery or translocation-molecule or moiety bound thereto or associated therewith. The delivery molecule may be a peptide or polypeptide, e.g., (a) HIV-TAT protein or a translocationally active derivative thereof, (b) penetratin having the sequence RQIKIWFQNRRMKWKK (SEQ ID NO:6), (c) a penetratin variant W48F having the sequence RQIKIFFQNRRMKWKK (SEQ ID NO:7)

(d) a penetratin variant W56F having the sequence RQIKIWFQNRRMKFKK, SEQ ID NO:8)

(e) a penetratin variant having the sequence RQIKIWFQNRRMKFKK, SEQ ID NO:9)

(f) herpes simplex virus protein VP22 or a translocationally-active homologue thereof from a different herpes virus such as MDV protein UL49; or (g) DelPep-1, having the sequence KETWWETWWTEWSQPKKKRKV (SEQ ID NO:10).

When a delivery moiety, such as the peptides and proteins discussed above, is fused to the biologically active peptide of the invention, it is preferred that the delivery moiety is N-terminal to the biologically active peptide.

In Vitro Testing of Compositions

The compounds of this invention are tested for their binding activity or their anti-apoptotic activity any one of the assays described and/or exemplified herein. The binding is preferably tested in a competition assay in which the peptide being tested is incubated with appropriate concentrations of soluble uPAR or uPAR-bearing cells or membrane preparations and Cav-1, and the binding of the uPAR material with the Cav-1 is measured in the presence vs. absence of the test peptide. Any other appropriate binding assays known in the art may be used.

The ability of the compounds of the invention to prevent apoptosis of may also be determined in assays measuring activation of caspase-3. Type I collagen (gelatin) is used to coat a P100 plate and $5 \times 10^5$ epithelial cells are seeded in EGM containing 10% FBS. After 24 hours (at 37° C. in 5% $CO_2$) the medium is replaced by EGM containing 2% FBS, 10 ng/ml bFGF and the desired test compound. The cells are harvested after 6 hours, cell lysates prepared in 1% Triton and assayed using the EnzChek® Caspase-3 Assay Kit #1 (Molecular Probes) according to the manufactures' instructions.

In Vivo Testing of Compositions

The ability of a test peptide (such as a functional variant of PP-1 or PP-2, or a peptide multimer to protect LECs from apoptotic effects of bleo treatment as described herein is a preferred test for assessing the functional activity of the peptide. Other tests known in the art that measure the same type of activity may also be used.

Method of Preventing or Treating Lung Injury or Fibrosis

The compositions described above are used in method to inhibit apoptosis of lung epithelial cells in vitro or in vivo, and to treat diseases or conditions associated with ALI and the subsequent pulmonary fibrosis.

Pharmaceutical and Therapeutic Compositions and Their Administration

The compounds that may be employed in the pharmaceutical compositions of the invention include all of the peptide/polypeptide compounds described above, as well as the pharmaceutically acceptable salts of these compounds. Pharmaceutically acceptable acid addition salts of the compounds of the invention containing a basic group are formed where appropriate with strong or moderately strong, nontoxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

As stated above, the compounds of the invention possess the ability to inhibit apoptosis and are exploited in the treatment of acute lung injury and, in particular, any fibrosis that follows.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in Gennaro, A R, *Remington: The Science and Practice of Pharmacy*, Lippincott Williams & Wilkins Publishers; 21$^{st}$ Ed, 2005 (or latest edition).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the treatment of any of a number of animal genera and species, and are equally applicable in the practice of human or veterinary medicine. Thus, the pharmaceutical compositions can be used to treat domestic and commercial animals, including birds and more preferably mammals, most preferably humans.

The term "systemic administration" refers to administration of a composition or agent such as the peptide described herein, in a manner that results in the introduction of the composition into the subject's circulatory system or otherwise permits its spread throughout the body, such as intravenous (i.v.) injection or infusion. "Regional" administration refers to administration into a specific, and somewhat more limited, anatomical space, such as instillation in the lung, the preferred route, or intraperitoneal, intrathecal, subdural, or to a specific organ. Other examples include intranasal, which is one route that corresponds to instillation in the lungs, intrabronchial, intra-aural or intraocular, etc. The term "local administration" refers to administration of a composition or drug into a limited, or circumscribed, anatomic space, such as subcutaneous (s.c.) injections, intramuscular (i.m.) injections. One of skill in the art would understand that local administration or regional administration often also result in entry of a composition into the circulatory system, i.e., so that s.c. or i.m. are also routes for systemic administration. Instillable, injectable or infusible preparations can be prepared in conventional forms, either as solutions or suspensions, solid forms suitable for solution or suspension in liquid prior to injection or infusion, or as emulsions. Though the preferred routes of administration are regional (into the lungs), the pharmaceutical composition may be administered systemically or topically or transdermally.

Other pharmaceutically acceptable carriers for compositions of the present invention are liposomes, pharmaceutical compositions in which the active polypeptide is contained either dispersed or variously present in corpuscles consisting of aqueous concentric layers adherent to lipidic layers. The active polypeptide is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired.

Therapeutic Methods

The methods of this invention may be used to inhibit acute lung injury and fibrosis in a subject in need thereof, by inhibiting epithelial cell death and its sequelae. The active peptide or variant of pharmaceutically acceptable salt thereof is preferably administered in the form of a pharmaceutical composition as described above.

Doses of peptide/polypeptides preferably include pharmaceutical dosage units comprising an effective amount of the peptide/polypeptide. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects By an effective amount is meant an amount sufficient to achieve a regional concentration or a steady state concentration in vivo which results in a measurable reduction in any relevant parameter of disease.

The amount of active compound to be administered depends on the peptide/polypeptide or variant selected, the precise disease or condition, the route of administration, the health and weight of the recipient, the existence of other concurrent treatment, if any, the frequency of treatment, the nature of the effect desired, for example, inhibition of tumor metastasis, and the judgment of the skilled practitioner.

A preferred single dose, given once daily for treating a subject, preferably a mammal, more preferably human who his suffering from or susceptible to ALI or fibrosis resulting therefrom is between about 0.2 mg/kg and about 250 mg/kg, preferably between about 10 mg/kg and about 50 mg/kg, for example, via instillation (by inhalation). Such a dose can be administered daily for anywhere from about 3 days to one or more weeks. Chronic administration is also possible, though the dose may need to be adjusted downward. The foregoing ranges are, however, suggestive, as the number of variables in an individual treatment regime is large, and considerable excursions from these preferred values are expected.

For continuous administration, e.g., by a pump system such as an osmotic pump that was used in some of the experiments described below, a total dosage for a time course of about 1-2 weeks is preferably in the range of 1 mg/kg to 1 g/kg, preferably 20-300 mg/kg, more preferably 50-200 mg/kg. After such a continuous dosing regiment, the total concentration of the peptide is preferably in the range of about 0.5 to about 50 µM, preferably about 1 to about 10 µM.

An effective concentration of the polypeptide for inhibiting or preventing inhibiting apoptosis in vitro is in the range of about 0.5 nM to about 100 nM, more preferably from about 2 nM to about 20 nM. Effective doses and optimal dose ranges may be determined in vitro using the methods described herein.

Having now generally described the invention, the same will be more readily understood through reference to the following examples which are provided by way of illustration, and are not intended to be limiting of the present invention, unless specified. The examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 2A:
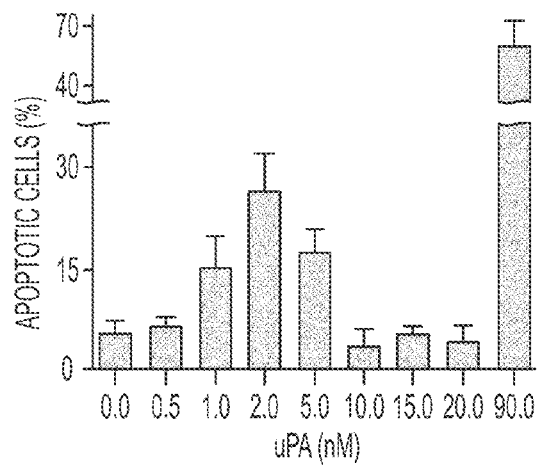
FIGS. 2A-2B is a set of graphs showing dose-dependent induction of primary small airway epithelial (SAE) cell apoptosis and proliferation by uPA.
Figure 2B:
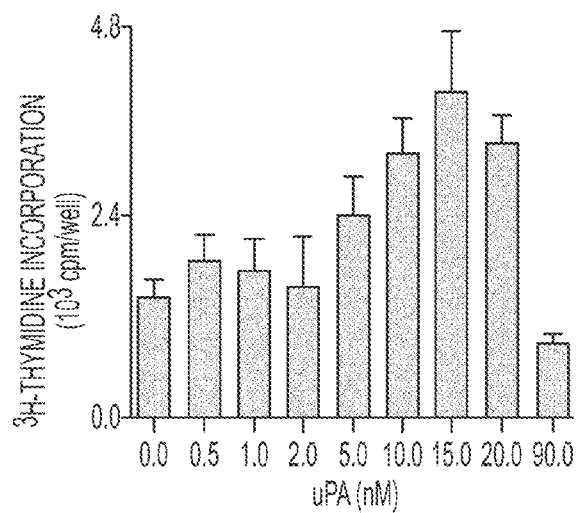

EXAMPLE I uPA Induces Dose-Related Apoptosis and Proliferation of Lung Epithelial Cells uPA treatment of primary small airway epithelial (SAE) cells in vitro for 48 hours induced apoptosis with an inverted U-shaped dose-response curve over a range of 0.5-20 nM. Cell proliferation is also induced by concentrations of between 5 and 20 nM. The apoptotic effects were weaker than those of bleomycin which did not induced, but rather inhibited cell proliferation. These results appear in FIGS. 2A-2B.

Figure 3:
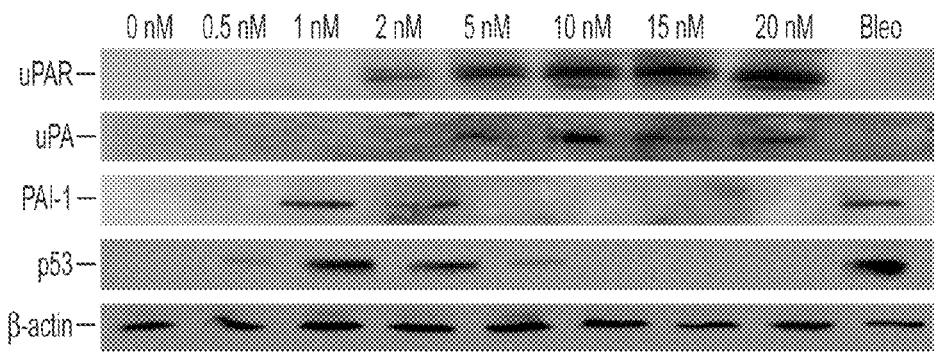
FIG. 3 is a Western blot showing that uPA induces dose-dependent apoptosis or proliferation of SAE cells. Then cells were treated with 0-20 nM of uPA for 24 h and uPAR, uPA, PAI-1 and p53 expression was determined by Western Blotting.

Western blots were made of extracts of uPA treated cells obtained 24 hours after the uPA was added. Results in FIG. 3 show that both uPA and uPAR expression was induced whereas PAI-1 and p53 expression was suppressed.

EXAMPLE II

The Effect of Bleo on LEC uPA, uPAR, PAI-1 and p53 Expression In Vitro

Figure 4:
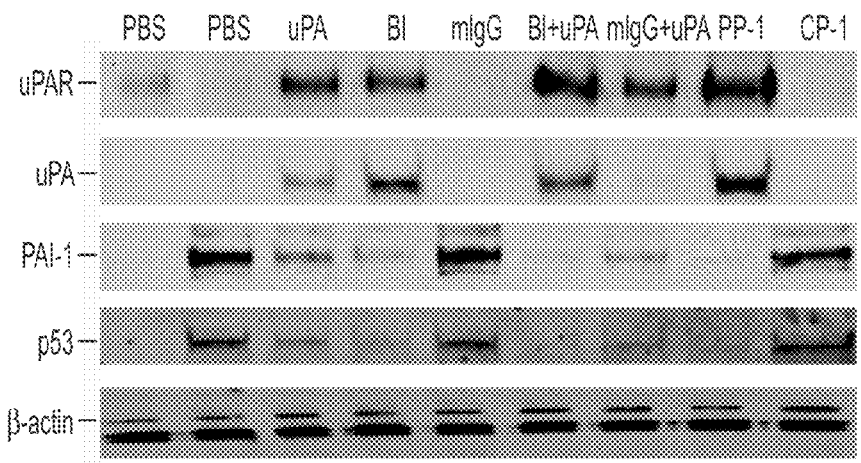
FIG. 4 depicts a set of Western blots showing the show the effect of bleo on uPA, uPAR, PAI-1 and p53 expression in LEC in vitro.

Beas2B cells were treated for 28 h with PBS or 40 µg/ml of bleo in the presence or absence of uPA or its ATF (20 nM), anti-β1-integrin monoclonal antibody (B1), (which activates β1-integrin by clustering), mouse IgG (mIgG), uPA+B1, uPA+mIgG, PP-1 (10 nM), or scrambled control peptide CP-1 (10 nM) at 37° C. In the case of uPA and PAI-1, the full length uPA was substituted with ATF, because uPA-mediated autoinduction or induction of PAI-1 occurs via the interaction of the ATF with uPAR (3-4). The cell lysates (CL) were analyzed for uPA, PAI-1, p53 and β-actin expression by Western blotting using specific antibodies. The membrane proteins were subjected to Western blotting using anti-uPAR antibody. The same responses of PAI-1 and uPA were seen in the conditioned medium (CM) by Western blotting (not shown). Alternatively, immunoprecipitation of cells labeled with $^{35}$S-methionine showed the same patterns of protein expression, indicating that synthesis of uPA, uPAR, PAI-1 and p53 was affected identically by the treatment conditions (not shown). Results are shown in FIG. 4.

Bleo induced both p53 and PAI-1 expression while suppressing uPA and uPAR in Beas2B cells.

EXAMPLE III

Induction or Suppression of Lung or BAL Protein Expression by Bleomycin and Effects of PP-1

Mice were treated intranasally with 50 µl saline or an equal volume of a 40 µg bleomycin solution. After 24 h, 10 mM PP-1 or the same concentration of control peptide CP-1 were given intraperitoneally using a 0.1 ml osmotic pump. Lungs were excised on day 7.

Lung tissue was chopped into small pieces with fine scissors and rinsed 3× with PBS. The tissues were then homogenized in 1 ml of extraction buffer (25 mM Tris-HCl, pH 7.9. 0.5 mM EDTA and 0.1 mM PMSF) and the homogenate was centrifuged at 12,000 g for 15 min at 4° C. The supernatant was removed and referred to as the crude extract. Protein content was measured using a BioRad protein assay kit. Cytosolic proteins were separated by SDS-PAGE and transferred to a nitrocellulose membrane which was blocked with 1% BSA in a wash buffer for 1 h at room temperature followed by overnight incubation with antibodies specific for uPA, PAI-1 or p53 in the same buffer at 4° C. Protein was detected by enhanced chemiluminescence (ECL). Membranes were stripped and immunoblotted for β-actin.

After preparation of the cytosolic extract, above, the pellet obtained after the initial centrifugation was resuspended in a membrane extraction buffer containing β-D-glucopyranoside and the suspension was homogenized for 5 to 10 min. The homogenate was allowed to mix (by rotation) at 4° C. for 2 h (Ref. 2). The homogenate was then centrifuged at 12,000 g for 30 min. The resulting clarified supernatant was analyzed for uPAR expression by Western blotting with anti-uPAR antibody and detected by ECL.

Figure 5:
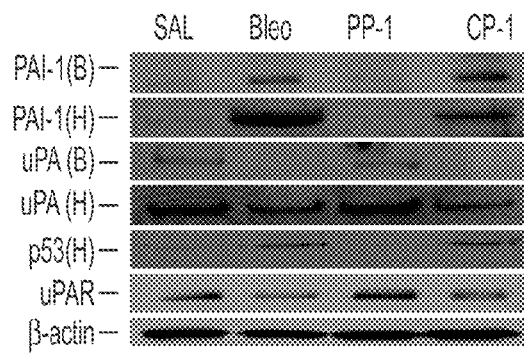
FIG. 5 is a series of Western blots showing that PP-1 altered bleomycin-induced p53, PAI-1, uPA and uPAR protein expression in mouse lungs. Mice were treated intranasally with 50 μl saline (SAL; control) or an equal volume of a 40 μg bleomycin solution (Bleo). After 24 h, 10 mM PP-1 ("Bleo+PP-1") or control peptide (Bleo+CP-1) were given intraperitoneally using a 0.1 ml osmotic pump. Lungs were excised on day 7, bronchoalveolar lavage (BAL) fluid ("B"), lung homogenates ("H") and membrane proteins (uPAR) were analyzed by Western blotting using antibodies specific for the murine proteins. (The same blot ("H") was then stripped and analyzed for β-actin confirm equivalent loading of the lanes)

Results are shown in FIG. 5. Mice were treated intranasally with saline (controls) are indicated (SAL). Mice receiving an equal volume of a 40 μg bleomycin solution are indicated (Bleo). Mice given PP-1 are indicated (PP-1) and those given control peptide are indicated (CP-1). BAL fluid is indicated (B), and lung homogenates (H) and membrane proteins (uPAR). Blots were probed with antibodies specific for the relevant murine proteins. (The same blot (H) was later stripped and analyzed for β-actin confirm equivalent loading of the lanes)

Bleomycin caused
(a) increased in PAI-1 in BAL fluid,
(b) increased PAI-1 and p53 in lung homogenates and
(c) suppression of uPA and uPAR.

Treatment of with PP-1 inhibited the increased p53 and PAI-1 expression and enhanced the suppressed uPA and uPAR levels. Similar results were obtained in mice into which the peptides were administered i.v.

Based on these in vivo results and results obtained in vitro using cultured cells shown above, it was concluded that that lung epithelial cell apoptosis depends upon induction of PAI-1 by increased p53 expression following bleomycin-induced damage. These events appear critical for the subsequent development of lung fibrosis and are reversed or prevented by PP-1.

EXAMPLE IV

Figure 6:
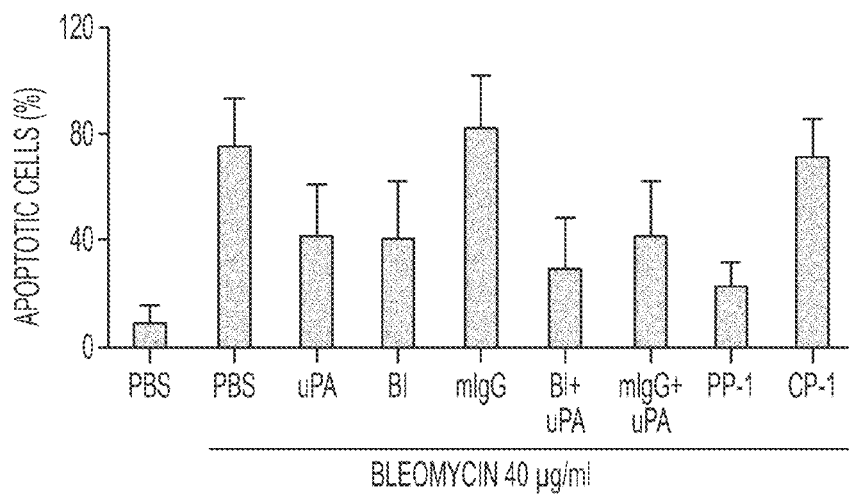
FIG. 6 is a graph showing apoptosis (% apoptotic cells) after treatment of cells with a β1-integrin activator (anti-β1-integrin antibody), uPA, a combination of the antibody and uPA, or PP-1, along with appropriate controls. Beas2B cells were treated for 28 h with PBS or 40 μg/ml of Bleo in the presence or absence of uPA (20 nM) or PBS as control, with anti-β1-integrin antibody (1 μg/ml, B1), or mouse IgG (mIgG) as control, a combination of the antibody (or control antibody) with uPA, and with PP-1 peptide (10 nM) or the CP-1 control peptide (10 nM) as described above at 37° C. Cells were harvested after trypsinization and LEC apoptosis was determined by flow cytometry after exposing the cells to anti-Annexin-V antibody and propidium iodide (as described for FIG. 2A).

Rescue of Epithelial Cells from Bleo-Induced Apoptosis by Activating β1-Integrin Expression of p53 and PAI-1 shown in Example I were correlated with LEC apoptosis induced by bleo (FIG. 6). Treatment with anti-integrin β1 antibody, uPA (20 nM), a combination of the antibody and uPA, and PP-1 protected LECs from bleo-induced apoptosis when compared to appropriate controls. Beas2B cells were treated for 28 h with PBS or 40 μg/ml of bleo (Bleo) with uPA (20 nM), and/or anti-β1-integrin antibody (1 μg/ml, B1), control mouse IgG (mIgG) PP-1 peptide (10 nM) or CP-1 control peptide (10 nM) as described above at 37° C. Cells were trypsinized and LEC apoptosis was determined by flow cytometry after exposing the cells to anti-Annexin-V antibody and propidium iodide (as described for FIG. 2A). These results were confirmed with TUNEL staining of cells cultured in cavity slides or by DNA laddering, with identical results (not shown).

These studies showed that activation of β1-integrin by anti-β1 antibody, treatment with uPA or PP-1 treatment rescued LECs from bleo-induced apoptosis. It is noteworthy that PP-1 was more potent in protecting LECs than was uPA or anti-β1-integrin antibody.

EXAMPLE V p53 Expression, Epithelial Apoptosis and ALI uPA-deficient uPAR-deficient PAI-1-deficient and P53-deficient Mice uPA-deficient, uPAR-deficient, p53-deficient and PAI-1 deficient mice are compared to wild type mice for effects of Bleo-treatment on epithelial apoptosis, lung inflammation, and lung fibrosis.

The extent of acute lung injury (ALI) is assessed by lung histology and determination of BAL protein, WBC and differential white cell counts are used to assess lung inflammation at selected intervals. Total lung collagen content is assessed using total lung hydroxyproline, and the distribution of lung collagen is determined by Trichrome staining. Total lung desmosine content is assessed as a measure of elastin. Morphometry is used to assess lung inflammation and scarring (97-100).

Using this range of established techniques, changes in expression of the p53, uPA, uPAR and PAI-1 antigens during the course of bleo-induced ALI or fibrosis were determined and the relationship between the proteins or p53 interactions with the transcripts occurring in the lung epithelium relates to the survival or apoptosis of the epithelial cells were examined. (See other Examples Bleo induces relatively greater p53 expression, epithelial apoptosis and ALI in wild type, uPA-deficient and uPAR-deficient mouse lung tissues compared to PAI-1 -deficient or p53-deficient mice (see Table 1). Bleo-challenged wild-type mice will express less LEC uPA and uPAR compared to p53-deficient mice due to lack of inhibition of uPA and uPAR by p53. These animals are expected to demonstrate increased LEC apoptosis versus the wild-type animals. The extent of ALI and subsequent fibrosis will increase in wild-type versus p53-deficient animals as a result. On the contrary, wild-type mice will express more PAI-1 than p53-deficient mice, based on initial results described in the other examples (see also FIG. 1). and will therefore exhibit relative increases in epithelial apoptosis, ALI and subsequent fibrosis.

Thus, bleo treated wild type mice exhibit more p53-uPA, uPAR and PAI-1 mRNA interaction compared to vehicle treated control samples from bleo-treated animals which will correlate with reduced uPA, uPAR and increased PAI-1 protein and mRNA, and p53 protein expression in these samples.

Bleo treated uPA- and uPAR-deficient animals will exhibit maximum p53-PAI-1 mRNA interaction which will parallel increased LEC apoptosis. PAI-deficient animals exposed to bleo will display p53-uPA or-uPAR mRNA interaction. The increased ALI and fibrosis in p53-deficient animals will occur as a result of failed apoptosis of damaged lung epithelium. The anticipated results are illustrated in Table 1.

TABLE 1

Anticipated Epithelial Apoptosis and Tissue Responses of Bleo-treated WT and uPA, uPAR, PAI-1 and p53 Knock-out Mice

| Knockout mice | Epithelial Apoptosis | Acute inflammation | Fibrosis |
| --- | --- | --- | --- |
| uPA$^{-/-}$ | +++ | +++ | +++ |
| uPAR$^{-/-}$ | +++ | +++ | +++ |
| p53$^{-/-}$ | --- | --- | --- |
| PAI-1$^{-/-}$ | --- | --- | --- |

(−): less response compared to Bleo treated wild-type controls;
(+): more response compared to Bleo-treated wild type controls.

EXAMPLE VI

PP-1 Administer In Vivo Protects Against Bleo-induced Apoptosis

In bleo-induced lung injury, p53 (67) and PAI-1 (25-27) increase in the lungs and LEC death is increased, supporting a link between ALI, p53 and the fibrinolytic system.

Figure 7:
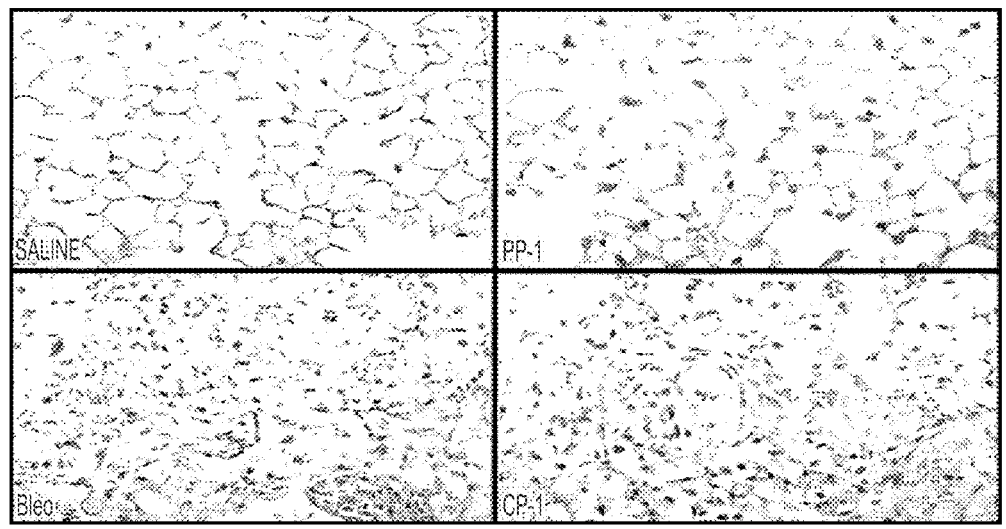
FIG. 7 is a set of four photomicrographs of lung tissue showing that. PP-1 prevents bleo-induced mouse lung injury. Mice were treated with saline (normal controls), bleo (50 μg/ml) by intranasal instillation. PP-1 (labeled as PP in the Figure) or CP-1 (labeled as CP in the Figure) were administered intranasally at a dose of 3.35 μM (375 μg/50 μl) on day 2, 4 and 6 after bleo. After 21 days the lungs were excised, inflated and fixed in formalin. 5 μM sections were subjected to TUNEL staining for apoptosis.

Results in FIG. 7 showed that. PP-1 prevented bleo-induced mouse lung injury in vivo. Mice were treated with saline (normal controls; upper right panel), bleo (50 μg/ml; lower left panel) by intranasal instillation. PP-1, upper right panel) or CP-1, lower right panel) were administered intranasally at a dose of 3.35 μM (375 μg/50 μl) on day 2, 4 and 6 after bleo. This equated to a dose on each day of about 19 mg/kg body weight. After 21 days the lungs were excised, inflated and fixed in formalin. 5 μM sections were subjected to TUNEL staining for apoptosis. These stained sections appear in FIG. 7.

Alternatively, PP-1 or CP-1 were administered in a continuous manner by i.p. implantation of an 0.1 ml osmotic minipump filled with PP-1 or CP-1 (10 mM or 2.92 mg/100 μl) one day after intranasal instillation of bleo. Lungs were harvested after 16 days. Total dose administered over that period was about 147 mg/kg. The apoptotic scores were calculated by counting the number of apoptotic cells in each field. Genomic DNA was isolated from saline, bleo, Bleo+ PP-1 or Bleo+CP-1 mouse lung extracts, and subjected to DNA fragmentation. PP-1 was found to protect against bleo-induced LEC apoptosis and DNA fragmentation. Peptides administered intranasally or via osmotic pump provided same degree of protection as shown in FIG. 7.

Figure 8:
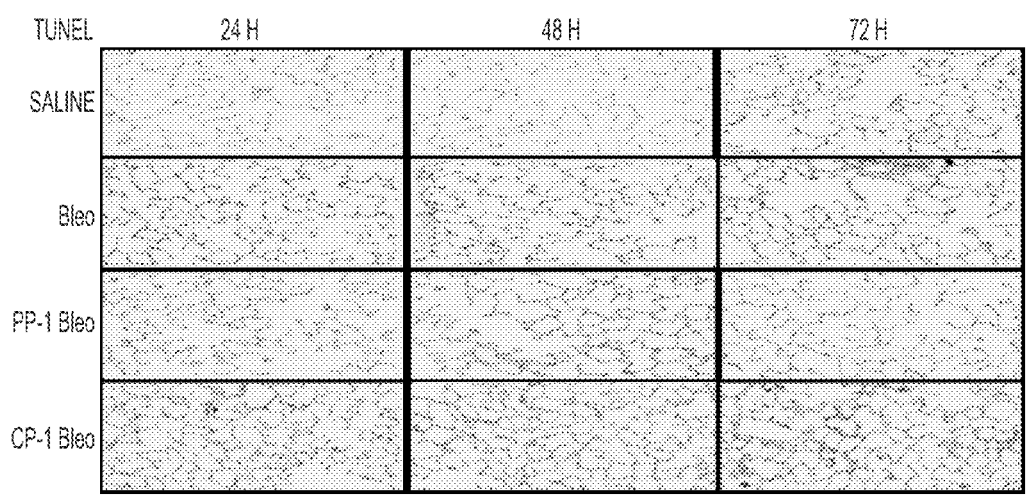
FIG. 8 is a set of photomicrographs of lung tissue showing that PP-1 prevented bleomycin-induced lung epithelial cell (LEC) apoptosis in vivo. Mice injected ip with PP-1 (4.5 μM) or control peptide (CP-1) on day 1 and 2, and treated with bleomycin (40 μg/50 μl) by intranasal instillation on day 2. The mice were sacrificed 24, 48 and 72 h later. Lungs were excised, inflated and fixed in formalin, and 5 μM sections were analyzed by TUNEL staining.

Results of additional studies (FIG. 8) show that bleomycin treatment increased apoptosis (TUNEL positive cells) as early as 24 h after exposure and this continued to increase over the following two days. Treatment with PP-1, but not with control peptide, reversed bleomycin-induced apoptosis. Similar results were obtained when the PP-1 and CP-1 were administered i.v.

These observations were independently confirmed by measurement of caspase 3 activation and degradation of poly (ADP-ribose) polymerase (PARP)

For immunohistochemical (IHC) analysis, lungs were inflated at constant pressure of 20 cm $H_2O$, removed and fixed overnight in 2% paraformaldehyde in PBS. Tissue was dehydrated by passage through a standard alcohol series and was embedded in paraffin. 5 μm sections were deparaffinized with xylene followed by incubation with 100% and 95% alcohol. After 10 min of antigen retrieval, the slides were incubated with $H_2O_2$ for 30 min to quench endogenous peroxidase. Slides were incubated overnight with the respective antibodies in PBS containing 0.1% Tween 20 and further processed using Lab vision kit (Freemont Calif.).

Figure 9:
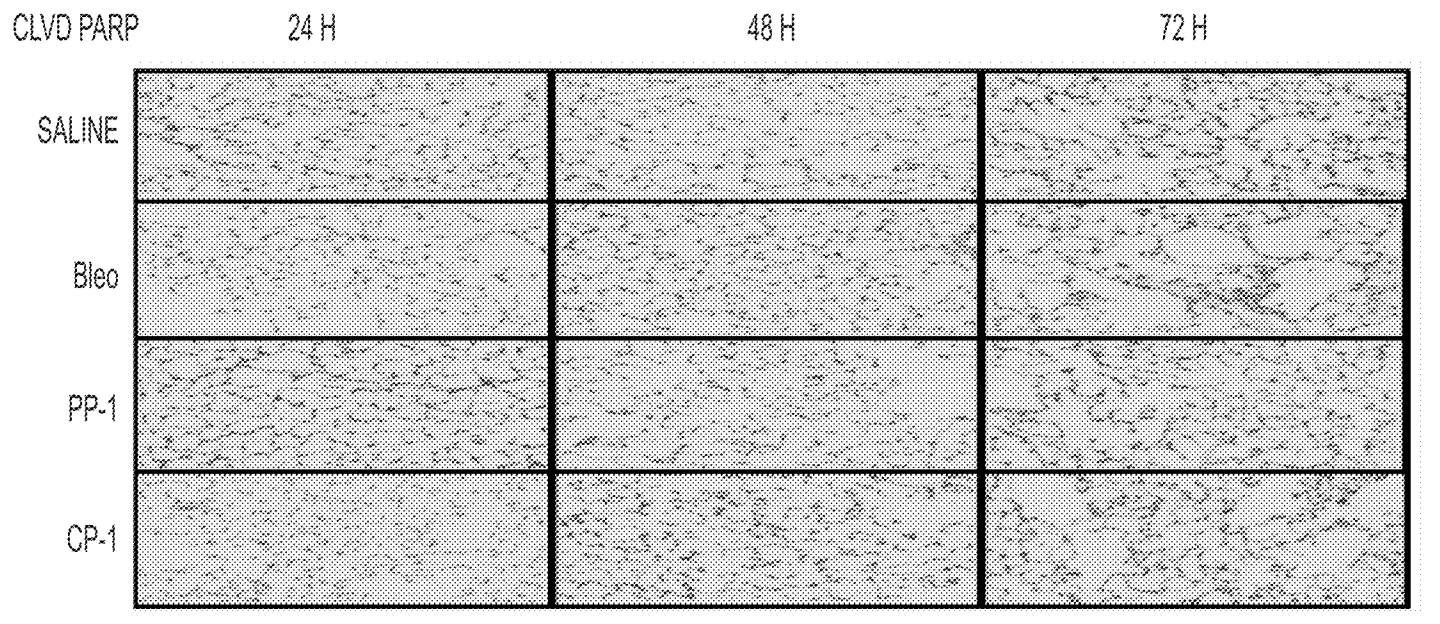

Results (FIG. 9) showed that bleomycin induced cleavage of PARP after 72 h of exposure. Treatment with PP-1 but not control peptide CP-1 reversed such PARP degradation. These observations were consistent with the apoptosis study discussed above (see New FIG. 1) and the results of caspase 3 activation (not shown).

An IHC study was conducted to analyze lung tissue for expression p53, uPA, uPAR, PAI-1 and cleaved caspase 3 (Table 2). Results showed that that bleomycin induced p53 expression beginning at 48 h and increasing up to 72 h. Peptide PP-1, but not control peptide CP-1, blocked bleomycin induced p53 expression; effects were apparent at around 72 h. These IHC observations were confirmed by Western blotting (see Example II and FIG. 5). PAI-1 expression was also increased in bleomycin-treated mice beginning 24 h after treatment. Treatment with PP-1 but not control peptide (CP-1) reduced this PAI-1 expression. uPA and uPAR levels fell between 48-72 h of bleomycin exposure. PP-1, but not control peptide CP-1 reversed this suppression.

TABLE 2

Relative Expression of p53, uPA, uPAR, PAI-1 and cleaved caspase3: IHC and TUNEL Analysis

| | 24 h | | | | 48 h | | | | 72 h | | | |
|---|---|---|---|---|---|---|---|---|---|---|---|---|
| | Sal | Bl | PP-1 | CP-1 | Sal | Bl | PP-1 | CP-1 | Sal | Bl | PP-1 | CP-1 |
| TUNEL | | | | | | | | | | | | |
| | + | + | + | ++ | + | ++ | + | +++ | + | ++ | + | +++ |
| Immunohistochemistry | | | | | | | | | | | | |
| p53 | + | + | + | ++ | + | + | + | ++ | + | ++ | + | +++ |
| PAI-1 | + | ++ | + | +++ | + | + | + | + | + | ++ | + | ++ |
| uPAR | + | + | + | + | ++ | + | ++ | + | ++ | + | ++ | + |
| Clvd PARP | + | + | + | + | + | + | + | + | + | +++ | + | +++ |
| Clvd Csp-3 | + | + | + | + | + | + | + | + | + | ++ | + | +++ |

J, °Abbrev:
Sal = saline;
Bl = bleomycin;
PP-1 = Bleo + PP-1'
CP-1 = Bleo + control peptide-1
Clvd = cleaved;
PARP = poly (ADP-ribose) polymerase;
Csp-3 = caspase-3

EXAMPLE VII

PP-1 and PP-2 Prevents Accumulation of Hydroxyproline or Desmosine in Bleo-Treated Lungs Lung tissue hydroxyproline (hpro) levels reflect collagen deposition and desmosine which reflects elastin content in lungs. Both serve as measures of lung fibrosis.

The hPro content of the whole mouse lungs tissues were measured using the technique of Woessner J F, 1961, *Arch. Biochem. Biophys.* 93:440-7). Lung tissue from each animal was homogenized in 1.0 ml of extraction buffer. One ml 12N HCl was added, and the samples were hydrolyzed at 110° C. for 24 h. After cooling, 5 μl of the samples were mixed with 5 μl of citrate-acetate buffer (5% citric acid, 1.2% glacial acetic acid, 7.25% sodium acetate and 3.4% sodium hydroxide) and 100 μl of chloramine-T solution (1.4% chloramine-T, 10% N-propanol, and 80% citrate acetate buffer) in 96 well plates. The mixture was incubated for 20 min at room temperature. A total of 100 μl of Ehrlich's solution (2.5 g p-dimethylaminobenzaldehyde added to 9.3 ml of n-propanol and 3.9 ml of 70% perchloric acid) was added to each well and the plates incubated at 65° C. for 18 min. The absorbance of each sample was measured at 550 nm. Standard curves were generated for each experiment using a known concentration of reagent hPro. Results were expressed as % changes in hPro content (with total hPro content of saline-treated control mouse lungs considered 100%).

Figure 10A:
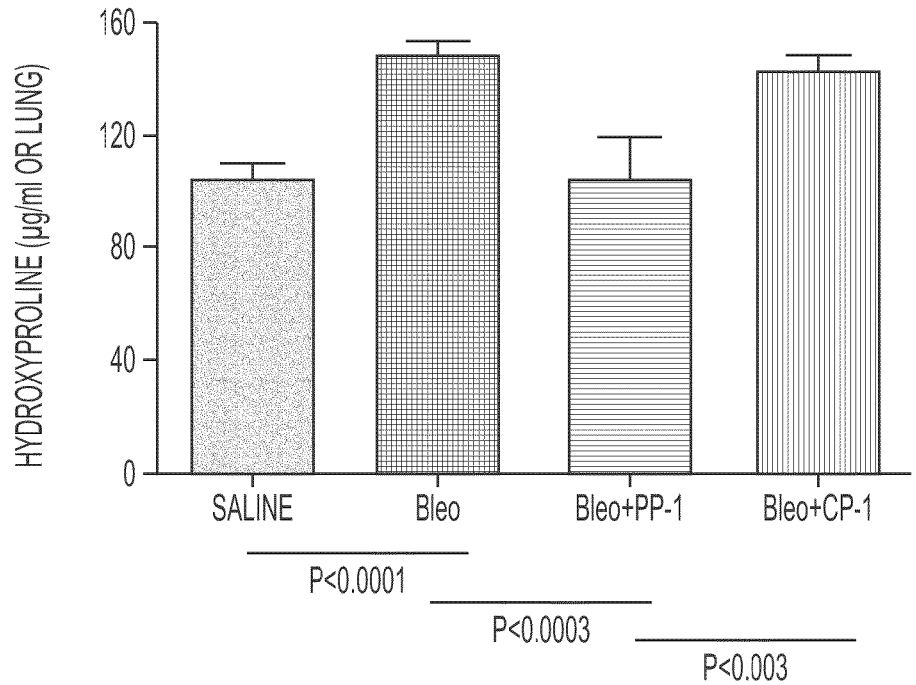
FIGS. 10A and 10B are graphs showing the effect of PP-1 on fibrosis following bleo-induced lung injury in the mouse.
Figure 10B:
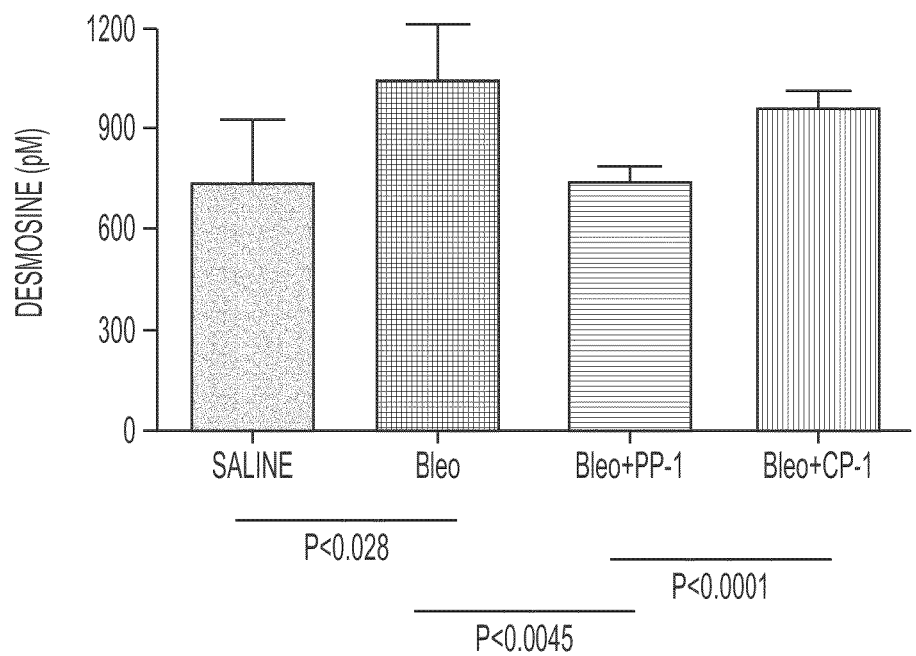

Lungs were harvested after 21 days, homogenized and the homogenates were subjected to the analysis of hydroxyproline as above (FIG. 10A) or desmosine (FIG. 10B). The effect of PP-1 on fibrosis in bleo-induced mouse lung injury was evaluated. Mice were treated with saline or 50 µg Bleo intranasally were implanted one day later with, 0.1 ml osmotic pumps i.p. The pumps were filled with either 10 mM (2.92 mg/100 µl) PP-1 ("Bleo+PP-1") or control scrambled peptide CP-1 ("Bleo+CP-1").

The study showed that bleo-induced fibrosis reflected as a significant increase in lung hydroxyproline or desmosine levels. This was significantly reduced, to normal levels by PP-1. CP-1 did not have this effect, and levels remained significantly elevated in lungs of CP-1 treated subjects.

Similar results were obtained when PP-1 or CP-1 were administered intranasally (as described in Example IV, above and FIG. 6).

Figure 11:
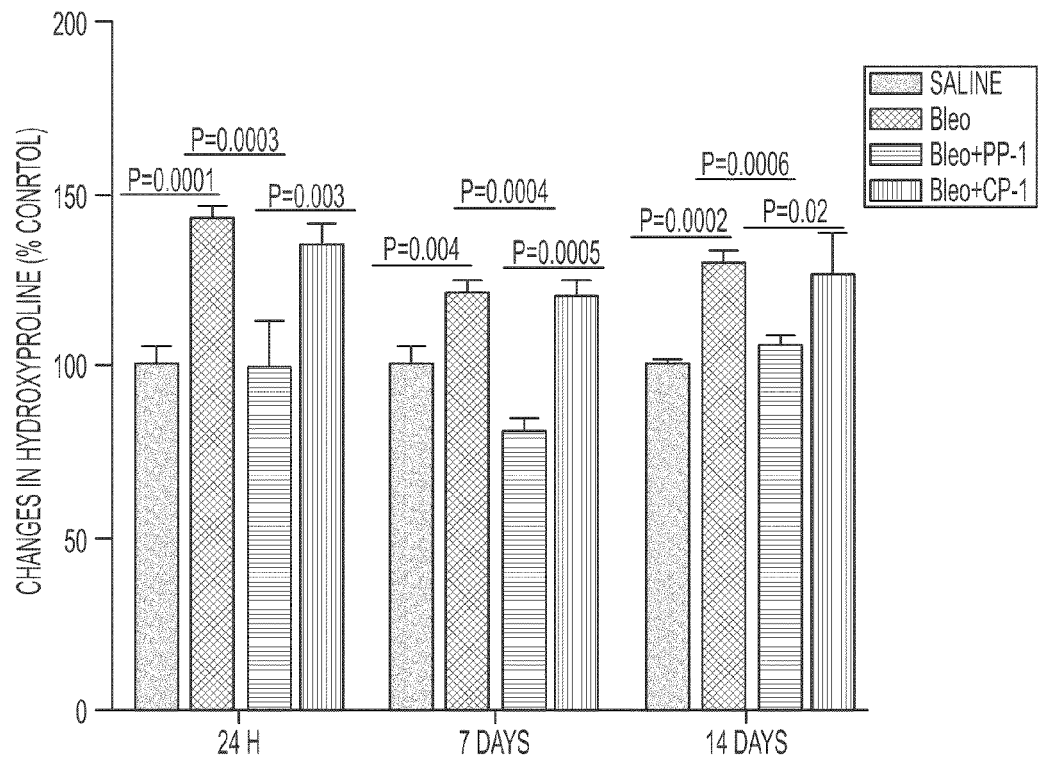
FIG. 11 is a graph showing that PP-1 but not control peptide CP-1 reversed bleomycin-induced increases in collagen deposition in lungs. Anesthetized mice received intranasal bleomycin HCl solution containing 40 μg/50μl in sterile saline solution. After 24 h, 7 days or 14 days 10 mM PP-1 ("Bleo+PP-1") or control peptide (Bleo+CP-1) were given ip using a 0.1 ml osmotic pump. Mice were sacrificed and lungs excised 21 days later. Lung homogenates were analyzed for hydroxyproline. Results are expressed a % of control hydroxyproline concentration.

Results in FIG. 11 showed that PP-1 significantly inhibited bleomycin-induced collagen deposition and lung fibrosis when administered before Bleo (prevention of injury) or after injury (therapy).

Figure 12:
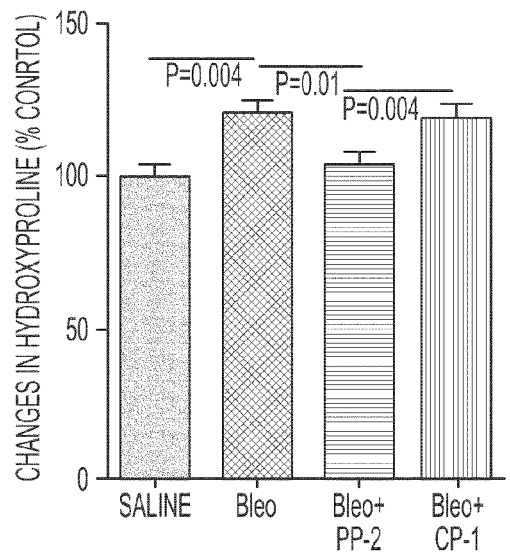
FIG. 12 is a graph showing that PP-2, but not its control peptide CP-2 reversed bleomycin induced increases in collagen deposition in the lungs. Anesthetized mice received intranasal bleomycin HCl solution containing 40 μg/50 μl in sterile saline solution. After day 7, 10 mM peptide PP-2 ("Bleo+PP-2") or control peptide ("Bleo+CP-2") were given intraperitoneally using a 0.1 ml osmotic pump. Lungs were excised after 21 days, lungs were homogenized and the homogenates were analyzed for hydroxyproline. Results are expressed a % of control hydroxyproline concentration.

A similar therapeutic study was conducted using the peptide PP-2 and its control peptide CP-2. The peptides were administered i.p. 7 days after induction of bleo injury (measured on lungs harvested 2 weeks later. Treatment with PP-2 significantly suppressed collagen deposition (measured as hPro content) when administered seven days after bleomycin injury (FIG. 12).

It was therefore demonstrated that PP-1 treatment before or after lung injury and PP-2 treatment after injury are potent inhibitors of pulmonary fibrosis that results from ALI, as modeled in the mouse by bleo-induced ALI and fibrosis.

p53 suppresses both uPA and uPAR mRNA stability by binding specifically to a 35 and 37 nt 3'UTR sequences respectively (10, 12). However, p53 interaction with a 70 nt PAI-1 mRNA binding sequence augments PAI-1 mRNA stability (11). These 3'UTR mRNA sequences show no homology to any other gene except that 37 nt p53 binding sequences of uPAR mRNA 3'UTR show partial homology to TNFα receptor. uPA induces uPA, uPAR and PAI-1 expression in a dose-dependent manner which is dependent on p53 expression. Publications from the inventors' group (2-5,7-12) and results presented herein support the conception set forth in FIG. 1.

Here, studies are done to determine whether these pathways are operative in the setting of bleo-induced epithelial injury. Expression of p53-binding sites competitively inhibited its interaction with endogenous uPA, uPAR and PAI-1 transcripts, induces uPA and uPAR while inhibited PAI-1 expression. The results (data not shown) provide a basis for the analysis described below.

The role of the p53 interaction with the 3'UTRs of the uPA, uPAR and PAI-1 mRNAs on uPA, uPAR and PAI-1 expression during bleo induced lung injury were determined (data not shown). This was done by over-expressing a chimeric cDNA containing p53 binding 35, 37 and 70 nt uPA, uPAR and PAI-1 mRNA 3'UTR sequences in Beas2B and primary SAE cells. The effect of expression of this chimera on LEC uPA, uPAR and PAI-1 protein and mRNA expression in the presence or absence of bleo are determined. Control cells are be transfected with a chimera incorporating non-p53-binding control sequences, vector-treated cells or nayve cells. If both uPA and uPAR protein, and mRNAs are induced while PAI-1 protein and mRNA suppressed by expression of the p53-binding chimera, its effect will be confirmed at the posttranscriptional level by assessing the stability of uPA, uPAR and PAI-1 mRNA by transcriptional chase experiments, as previously described (10-12, 104).

The p53 binding chimera competitively binds p53 and uPA and uPAR mRNA are stabilized while PAI-1 mRNA is destabilized (see schema shown in FIG. 1.

If the p53 binding chimera induces uPA and uPAR while suppressing PAI-1 via changes in mRNA stability, its overexpression will promote increased epithelial cell survival in bleo-treated cells. To confirm this, p53 binding or control non-binding sequences are expressed the in Beas2B or primary SAE cells which are then treated with or without bleo and its effect on LEC apoptosis determined, using conventional method described herein.

The present inventors have already found that p53 is induced by bleo-treatment of LECs in culture. However, cells expressing p53-binding 35, 37 and 70 nt uPA, uPAR and PAI-1 mRNA 3'UTR sequences are expected to resist bleo induced apoptosis compared to cells over-expressing non-p53-binding control sequences or empty vector-treated or naive controls.

Bleo treatment is expected to fail to suppress uPA and uPAR protein and mRNA and to express comparatively stable uPA and uPAR mRNAs. These cells also are expected to exhibit minimal amount of PAI-1 protein and mRNA expression, with PAI-1 mRNA being highly unstable.

EXAMPLE VIII

Inhibition of Collagen Deposition (Fibrosis) by PP-1

Figure 13:
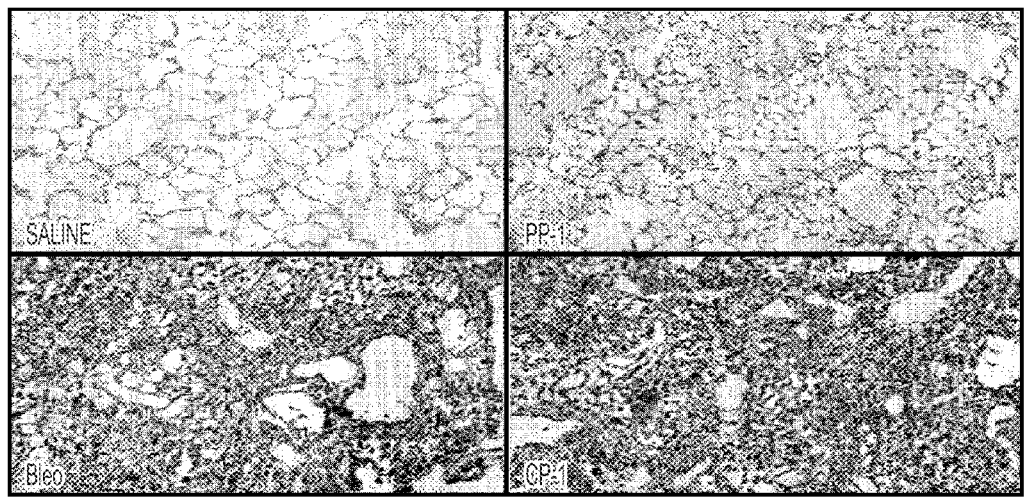
FIG. 13 is a set of photomicrographs showing that PP-1 prevents bleo-induced collagen deposition in mouse lung. Mice were treated with bleo (50 μg/ml) by intranasal instillation followed by treatment with PP-1 (10 nM) or control peptide CP-1 on day 2. Lungs were excised on day 21, inflated and fixed in formalin, a sectioned into 5 μM sections which were subjected to Mason's Trichrome stain (a three-color stain that stains cell nuclei red, collagen green or blue, and cytoplasm red). Blue staining indicates collagen deposition in bleo-treated lung sections. PP-1 prevented bleo-induced collagen deposition.

Collagen deposition in mouse lung after bleo treatment was investigated. Mice were treated with bleo (50 µg/ml) by intranasal instillation followed by treatment with PP-1 (10 nM) (designated as PP in Figure) or control peptide CP-1 (designated CP in FIG. 13) on day 2. Lungs were excised on day 21, inflated and fixed in formalin, a sectioned into 5 µM sections which were subjected to Mason's Trichrome stain (a three-color stain that stains cell nuclei red, collagen green or blue, and cytoplasm red).

The results (FIG. 13) show that PP-1 prevented bleo-induced collagen deposition, a measure of pulmonary fibrosis. This is further evidence of the ability of PP-1 to act as a prophylactic or therapeutic agent against ALI and fibrosis.

In a related model, injury is induced by treating with bleo as above. However, infusion of PP-1 or PP-2 is withheld until day 5, 14 or 21 to delineate a therapeutic effect from a preventative effect.

PP-1 treatment after day 5 or 14, times at which maximum p53 has been attained following bleo, prevents the development of fibrosis by blocking LEC death. However, when first given on day 21, PP-1 is less effective depending upon its ability to prevent fibroblast proliferation.

Results presented above showed the presence of apoptotic cells on day 21 in bleo-treated lung sections, indicating that LECs are continuously dying in such injured lungs. On this basis, PP-1 treatment commencing on day 21 could still be effective.

EXAMPLE IX

PP-1 and PP-2 Protect Lung Epithelium from Bleo-induced Injury and Fibrosis

A comparison was made of normal and bleo-treated lung, and the effect of PP-1 and PP-2 on the bleo-treated lungs were examined. Animals were treated with bleo and peptides as above. Lung tissue was removed at day 21 and stained with Mason's trichrome stain for collagen and subjected to TUNEL staining for apoptosis.

Figure 14A:
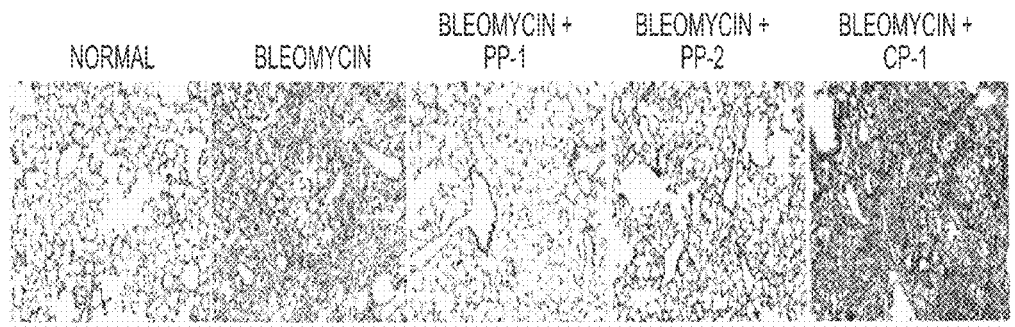
FIGS. 14A & 14B is a series of photomicrographs of lung epithelial tissue stained with Mason's trichrome stain for collagen (FIG. 10A) and by TUNEL staining for apoptosis (FIG. 10B). Bleo-treated animals were instilled with either PP-1, PP-2 or control peptide CP-1 one day after bleo treatment, The lungs were removed on day 21, subjected to the staining procedures and examined for collagen accumulation or apoptosis.
Figure 14B:
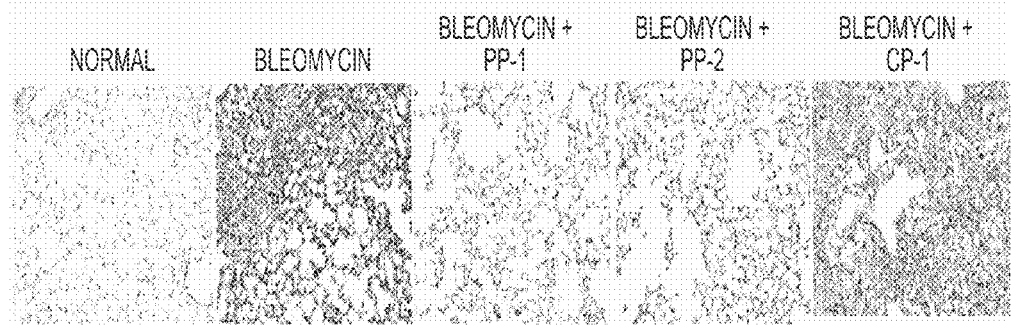

The histological results are depicted in FIGS. 14A and 14B. and are summarized in Table 3 below.

TABLE 3

| | Tissue Source (treatment group) | | | | |
|---|---|---|---|---|---|
| | Normal lung | Bleo | Bleo + PP-1 | Bleo + PP-2 | Bleo + CP-1 or CP-2 |
| Lung epithelial cell apoptosis | Normal cells 9% cell death | Fibrotic cells, 80% cell death | No fibrosis, 12% cell death | No fibrosis, 11% cell death | Fibrotic cells, 90% cell death |
| Collagen content in lung section | Normal | Increased | Normal | Minimal | Increased |
| Pathological observations | Normal cells | Foamy macrophages, organizing pneumonia, interstitial expansion | Normal cells with some early nodular area | Normal cells | Foamy macrophages, organizing pneumonia, interstitial expansion |

The following conclusions were reached:
(1) PP-1 protected LECs from bleo-induced lung injury by >90%
(2) PP-1 also prevented the development of bleo-induced lung fibrosis
(3) PP-2 protected LECs from bleo-induced lung injury
(4) PP-2 also prevented the development of bleo-induced lung fibrosis
(5) CP-1 or CP-2, a control peptide corresponding to the composition of PP-1 and PP-2 respectively, did not have any discernible effect on Bleo-damaged lung tissue

EXAMPLE X uPAR/β1-integrin Interactions Control Viability of LECs.

The signaling mechanisms by which uPA and the β1-integrin/uPAR complex regulates epithelial cell apoptosis or survival are not yet fully defined. uPAR associates with β1-integrin, the lipid raft protein Caveolin-1 (77-81), and the receptors GP130 and EGFR at the cell surface (90-94). This complex is linked to regulation of LEC viability. β1-integrin activation (by antibody clustering) inhibited p53 induction by bleo, induced uPA and uPAR expression, and concurrently suppressed PAI-1 expression and increased cell viability. β1-integrin activation therefore reversed LEC apoptosis and inhibited the pro-apoptotic factors p53 and PAI-1 (5,1 1). The combination of β1-integrin clustering and uPA (20 nM) additively reversed bleo-induced lung epithelial apoptosis. These findings implicated β1-integrin and coordinate changes in uPA, uPAR and PAI-1 in protection against LEC apoptosis and suggested that the mechanism operates in the pathogenesis of epithelial apoptosis induced by bleo challenge.

Evidence from others demonstrated direct association of uPAR with the lipid raft protein caveolin-1 (78, 81) further linking the β1-integrin and uPA to caveolin-1 and uPAR. As discussed in the background section, Cav-1 binds to Src kinase via the Cav-1 CSD (present PP-1) (107). Both uPAR and Cav-1 are required for association of active Src kinase with β1-integrins. Loss of Cav-1/β1-integrin association results in loss of ligand induced FAK phosphorylation and Src activation.

Figure 15:
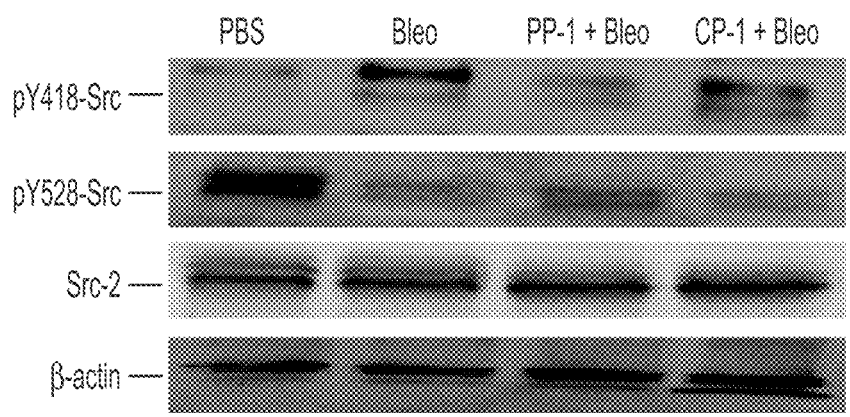
FIG. 15 is a series of Western blots showing that the effect of PP-1 on bleo-induced tyrosine phosphorylation of Src kinase in LECs. Beas2B cells treated with PBS or bleo (40 μg/ml) in the presence or absence of PP-1 or the control scrambled peptide CP-1 for 24 h. Cell lysates were analyzed for activating tyrosine (Y418) phosphorylation and inhibitory tyrosine (Y529) phosphorylation by Western blotting using phospho-specific antibodies. The same membrane was stripped and analyzed for total Src (Src-2) kinase and β-actin expression by Western blotting using specific antibodies.
Figure 16:
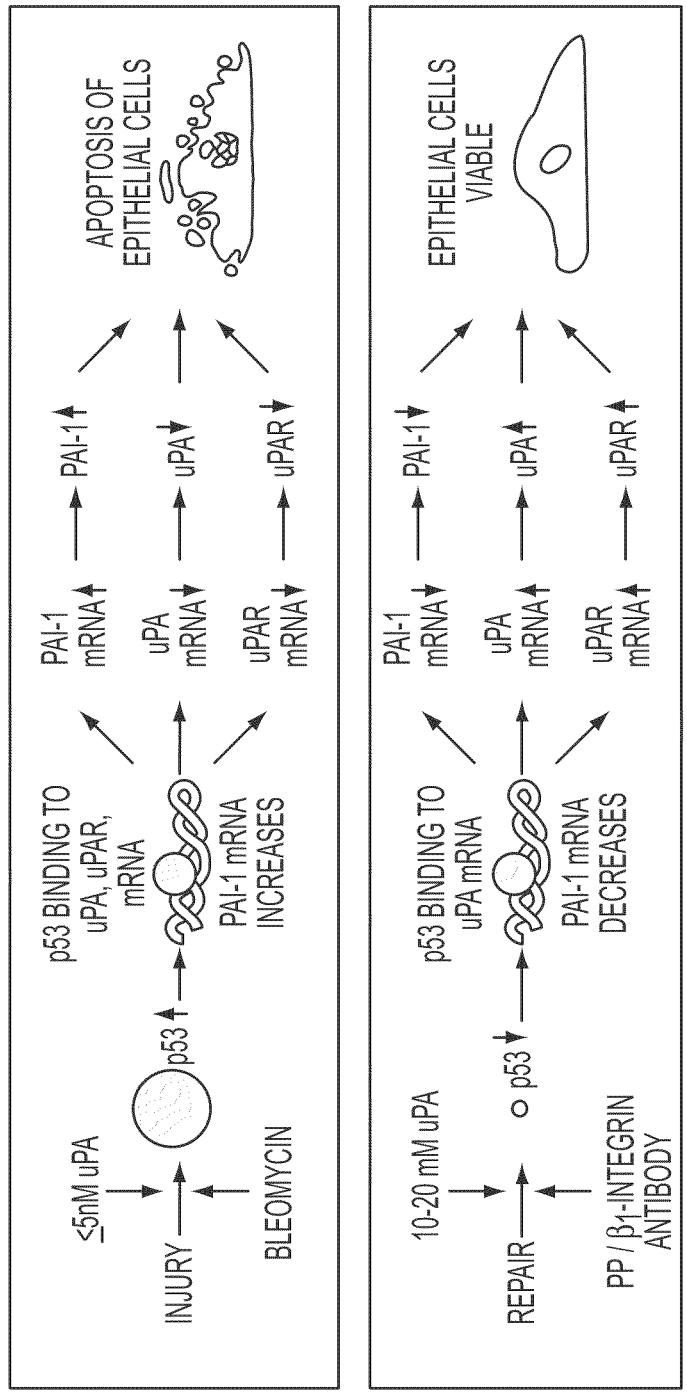
FIG. 16 is an illustrative depiction of lung injury and its repair. Relatively low dose uPA (<5nM) or bleomycin induce p53 which binds to uPA, uPAR and PAI-1 mRNA and inhibits uPA and uPAR while inducing PAI-1 expression (by posttranscriptional regulation of mRNA), resulting in LEC apoptosis. Inhibition of p53 expression through β1-integrin activation by integrin clustering or treatment with protective peptides (referred to collectively as "PP" but including PP-1, PP-2, variants, fusions, multimers, etc. as described in this document) or relatively high doses of uPA (e.g., 10-20 mM) induces uPA and uPAR while suppressing PAI-1 expression, providing protection against the apoptosis.
Figure 17:
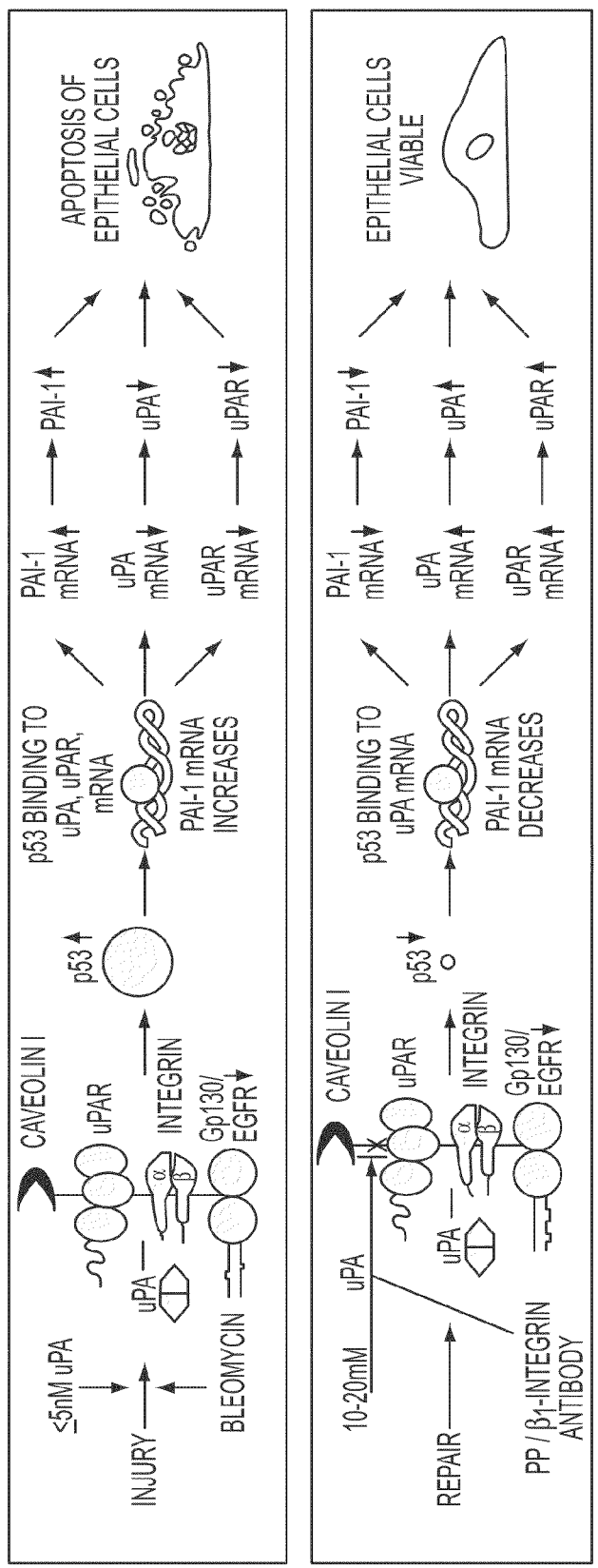
FIG. 17 is an illustrative depiction of lung injury resulting from bleo or relatively low concentrations of uPA (<5 nM). uPAR associated caveolin-1 interacts with β1-integrin-Gp130 or EGFR complexes which induce p53 which binds to uPA, uPAR and PAI-1 mRNA and inhibits uPA and uPAR while inducing PAI-1 expression (by posttranscriptional regulation of mRNA), resulting in LEC apoptosis. Inhibition of uPAR associated Cav-1 interaction with β1-integrin/Gp130/EGFR complexes by treatment with "PP" (see description of FIG. 16) or higher doses of uPA (e.g., 10-20 mM) induces and/or activates EGFR or GP130 which inhibit p53 expression by β1-integrin activation which increases uPA and uPAR levels while suppressing PAI-1 expression, providing protection against apoptosis.
Figure 18:
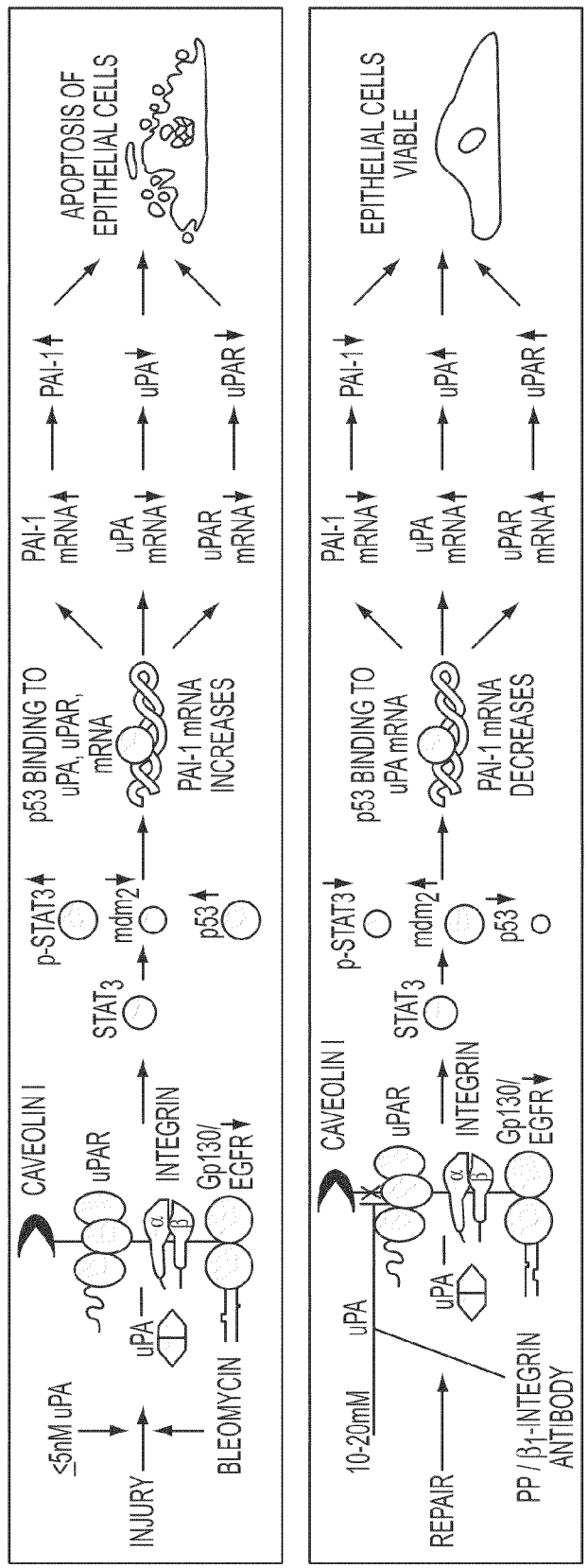
FIG. 18 is an illustrative depiction of lung injury by bleomycin or uPA (<5 nM). uPAR associated Cav-1 interacts with β1-integrin-Gp130 or EGFR complexes which prevents EGFR or GP130 or uPAR associated tyrosine phosphorylation (activation) of Stat3 which induces p53 which binds to uPA, uPAR and PAI-1 mRNA and inhibits uPA and uPAR, which induces PAI-1 expression (by posttranscriptional regulation of mRNA) which results in LEC apoptosis. Inhibition of uPAR associated Cav-1 interaction with β1-integrin/Gp130/EGFR complexes by treatment with "PP" (see description of FIG. 16 or relative high concentrations of uPA (e.g., 10-20 mM)) induces Stat3 activation which induces mdm2 which in turn accelerates p53 degradation. Inhibition of p53 increases uPA and uPAR while suppressing PAI-1 expression, providing protection against apoptosis.
Figure 19:
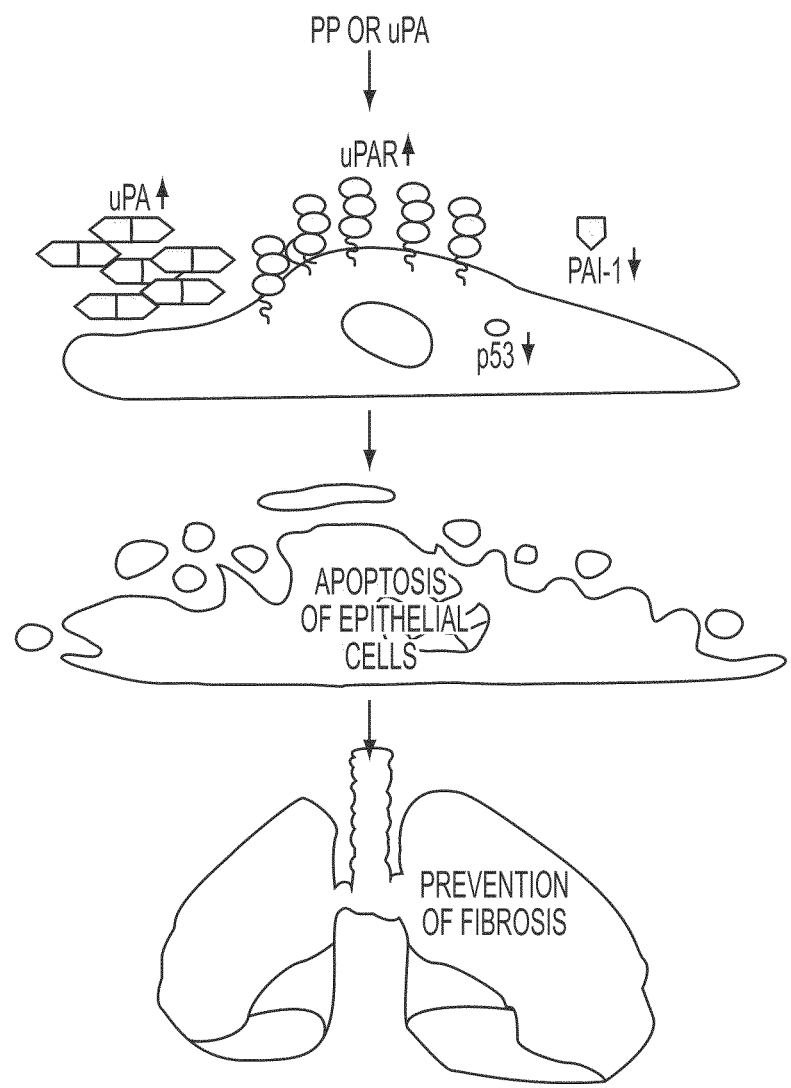
FIG. 19 is an illustrative depiction of the protective effects of "PP" (see description of FIG. 16) and of relatively high concentrations of uPA (>5 nM) on LEC apoptosis and prevention of fibrosis. These effects occur through inhibition of uPAR-associated Cav-1 interaction with β1-integrin/Gp130 or EGFR complexes (not depicted) which leads to induction of uPA and uPAR and inhibition of PAI-1, all of which lead to inhibit p53 and its injurious effects.

The results (FIG. 15) showed that
(1) bleo-induced Src kinase activation through phosphorylation of Src Y418
(2) PP-1 peptide that competes with Cav-1 binding inhibited bleo-induced activation of Src Y418 through phosphorylation of Src Y529
(3) This in turn prevented LEC apoptosis through inhibition of p53.

Treatment of LECs with uPA (results not shown) or anti-β1-integrin antibody induced time-dependent FAK phosphorylation, indicating that uPA mediates epithelial cell survival via activation of the FAK pathways. Thus, it was concluded that β1-integrin/uPAR/caveolin-1-associated Src activation plays a pivotal role in LEC p53 induction and apoptosis during bleo-induced injury.

uPAR lacks a cytoplasmic tail to transduce signals, and uPA increases the β1-integrin-uPAR interaction. Caveolin-1 is associated with uPAR/β1-integrin complexes (77-81, 105) which regulates Src activity of the β1-integrin (108-109).

According to the present invention, Cav-1 binds to Src kinases through the CSD and the Src interacting domain increases cell viability by increasing uPA and uPAR, and inhibiting p53 and PAI-1 expression in LECs. Therefore, signals transduced through β1-integrins regulate epithelial cell viability.

To test if signals transduced through the β1-integrin cytoplasmic tail are required for protection of LECs against bleo-induced apoptosis, the following β1-integrin chimeras are fused to the extracellular and transmembrane domain of the human CD2 antigen and expressed:
(1) chimeras with the intact cytoplasmic domain;
(2) deletion mutants lacking the membrane proximal motif which binds to FAK; and
(3) truncations lacking the distal p85 subunit of PI-3-K or ILK binding domain).

These chimeras lacking the ECD of β1-integrin so cannot be activated by anti-β1-integrin antibody.

The effect on β1-integrin activation by PP-1 and PP-2 (or anti-β1-integrin antibody or uPA) on uPA, uPAR, p53 and PAI-1 expression and on resistance of Beas2B LECs to bleo-induced apoptosis are determined. Resistance to apoptosis is measured by flow cytometry or DNA fragmentation (see supra) in cells expressing these chimeric constructs with or without bleo treatment. These responses are compared with those of appropriate control cells (untreated cells, cells treated with or saline (instead of bleo), CP-1 (as a control for PP-1), CP-2 (as a control for PP-2), and an isotypically matched immunoglobulin (as a control for the anti-β1-integrin antibody).

Expression of the chimeric domain containing the full length cytoplasmic tail of the β1-integrin functions as a dominant negative receptor and competes for endogenous kinases (FAK, PI-3-K or ILK) that bind to the β1-integrin cytoplasmic domain to transduce a signal (110-112). In these cells, PP-1 and PP-2 (or uPA or β1-integrin antibody) fail to inhibit p53 and induce more PAI-1 and, therefor, apoptosis, in response to bleo treatment.

These cells are expected to express less uPA and uPAR and be more apoptotic due to an inability to suppress p53 and PAI-1 and/or to activate FAK or PI-3-K or ILK (compared to untransfected or vector cDNA-transfected control cells). These cells are expected to be highly susceptible to apoptosis induced by bleo injury.

Cells that express
(a) the β1-integrin cytoplasmic domain (deletion mutant) lacking the FAK binding region which is necessary for tyrosine phosphorylation of FAK or
(b) a truncation mutant devoid of distal PI-3-K and/or ILK binding sequence required for Serine 473 phosphorylation of Akt,
regulate p53 expression as do controls following bleo treatment.

If cells expressing the proximal deletion mutant lacking FAK are found to reverse bleo induced Beas2B cell apoptosis following PP-1 or PP-2 (or anti-β1-integrin antibody or uPA) treatment, binding of FAK will be assessed for its role for this protection against apoptosis.

If distal truncation mutants lacking the PI-3-K or ILK domain affect either PP-1 or PP-2 (or anti-β1-integrin or uPA treatment), then P-I-3-K/Akt or ILK must be involved in resistance to apoptosis. Involvement of Src kinases in the tyrosine phosphorylation of FAK (77) strongly suggests that FAK is involved in p53 expression and protection of LECs following bleo treatment (See, also, FIG. 6).

EXAMPLE XI

The β1-integrin/FAK Pathway in PP-1 or PP-2-Mediated Protection of Epithelial Cell Apoptosis and p53 Expression If the above deletion study confirms involvement of FAK in bleo-induced apo1ptosis or PI-3-K/Akt or ILK signaling in protection against apoptosis following exposure to PP-1 or PP-2 (or exposure to β1-integrin antibody or uPA), the requirement for FAK or ILK or PI-3-K in PP-1- or PP-2- (or uPA-) mediated epithelial cell viability will be tested. This is done by sequentially inhibiting FAK or PI-3-K or ILK expression using siRNAs. Expression of p53 and subsequent downstream expression of uPA, uPAR and PAI-1 are also determined.

Susceptibility of LECs to bleo-induced apoptosis will increase in cells in which expression of FAK or PI-3-K or ILK is suppressed by siRNA. PP-1 and PP-2 (and anti-β1-integrin antibody or uPA will have a minimal or no protective effect here. uPA and uPAR expression are suppressed, and p53 and PAI-1 expression are induced.

However, in p53 SiRNA-treated cells, p53 and PAI-1 expression is inhibited and uPA and uPAR expression is induced so that these cells are resistant to bleo induced apoptosis.

These results lead to the conclusion that that (1) β1-integrin activation by PP-1 or PP-2 or their variants, multimers, etc. (or uPA or anti-β1-integrin antibody ligation) suppresses p53 which, in turn (2) protects LECs from bleo-induced apoptosis through induction of pro-survival proteins uPA and uPAR and inhibition of the pro-apoptotic protein PAI-1.

While signaling intermediates of the FAK or Akt pathway are known (109-113), the signaling intermediaries induced by PP-1 or PP-2 (or uPA or anti-β1-integrin antibody) are not known at this time. Since PP-1 (but not CP-1 or anti-β1-integrin antibody) inhibits bleo-induced p53 expression (5), PP-1 will be paired with CP-1 as positive and negative controls.

Determination of the Role of EGFR on PP-1/PP-2- (or uPA or Anti-β1-integrin Antibody)-Induced Epithelial Cell Survival The present inventors recently found that both uPA and anti-β1-integrin antibody induced tyrosine phosphorylation of the EGFR in LECs (not shown). Others reported that uPA causes a Src-dependent transactivation of EGFR which is independent of EGF binding (113-114). EGFR associates with uPAR/Caveolin/β1-integrin complexes (78-81, 105). EGFR directly interacts with scaffolding domain of caveolin-1 which inactivates EGFR signaling. Based on this, resistance of LECs to bleo induced apoptosis by PP-1 or PP-2 (or uPA or anti-β1-integrin antibody) is believed to utilize an intracellular signal transduction pathway through EGFR.

(a) Effect of the uPAR/Cav-1/EGFR Interaction on LEC Survival

The involvement of EGFR-mediated signaling in the protection induced by PP-1 or PP-2 (or uPA or anti-β1-integrin antibody) against bleo-induced p53 expression and LEC apoptosis is assessed.

After bleo treatment, Beas2B and other LECs will be exposed to PP-1 and PP-2 (or ~20 nM uPA (which suppresses p53) or anti-β1-integrin antibody. Expression, activation and interaction of EGFR with uPAR, Cav-1 and β1-integrin are determined by immunoprecipitation followed by Western blotting.

Increased EGFR-uPAR interaction with PP-1 or PP-2 (or uPA), will lead to suppression of p53 and increased LEC viability associated with increased uPA and uPAR expression. PP-1, PP-2 (and anti-β1-integrin antibody) are thus expected to block apoptosis.

Role of uPAR/β1-integrin/EGFR in PP-1/PP-2 or uPA-induced uPA, uPAR, p53 and PAI-1 Expression and LEC Survival:

Expression of EGFR inhibited by siRNA is used to evaluate the role of EGFR in uPA-induced uPA, uPAR, p53 and PAI-1 expression, and protection of LECs against bleo-induced apoptosis, The effect of PP-1 or PP-2 (or uPA or anti-β1-integrin antibody) p53 expression are evaluated by Western blots. As uPA is known to induce tyrosine phosphorylation of EGFR at Y845 (a Src kinase activation site) (113-114), tyrosine phosphorylation of EGFR will be inhibited by specific inhibitors and the effect of PP-1 or PP-2 (or uPA or anti-β1-integrin antibody) on bleo-induced p53 expression and resistance to apoptosis are determined. Since EGFR is involved in the activation of PI-3-K (115) and is associated with β1-integrin and uPAR complexes (116), cytoplasmic domains of various β1-integrin constructs are used as described above to determine the role of EGFR in PP-1- or PP-2-mediated LEC viability.

To directly test the involvement of EGFR in PP-1- or PP-2- (or uPA- or anti-integrin antibody-) mediated protection of LECs from bleo-induced apoptosis, Cav-1 will be inhibited with or without EGFR by siRNA or commercially available biochemical inhibitors, and the resistance to apoptosis assessed. The contribution of the expression of uPA, uPAR, p53 and PAI-1 to these responses will be tested as above. This will confirm the role of EGFR and Cav-1 in the regulation of LEC cell viability.

Role GP130 in uPA-induced p53 Expression and Epithelial Cell Proliferation:

As noted, the present inventors and colleagues recently found that uPA induces tyrosine phosphorylation (activation) of Stat3 in LECs (31). GP130 activates the JAK/Stat3 pathway and uPA binds to GP130 (92). Inhibition of Stat3 activation using DN mutant cDNA overexpression inhibits uPA-induced proliferation of LECs and enhances Beas2B cell apoptosis.

According to the present invention, improved epithelial cell survival and uPA, uPAR, p53 and PAI-1 expression, and Stat3 activation utilizes intracellular signal transduction going through GP130.

The effect of the uPA-GP130 interaction by PP-1 or PP-2 (or uPA or anti-β1-integrin antibody) on LEC viability will be evaluated. As was already found (results not shown) activation of β1-integrin by an anti-β1-integrin antibody or uPA induces GP130 in bleo-treated Beas2B cells. The involvement of GP130 in PP-1 or PP-2 (or 20 nM uPA or anti-β1-integrin antibody)-induced resistance to apoptosis or inhibition of p53 expression, is assessed by treating Beas2B and/or other LECs with PP-1 or PP-2 (or uPA or anti-β1-integrin antibody) in the presence or absence of bleo and determining expression, activation and interaction of GP130 with uPAR/Caveolin-1/β1-integrin by Western blot analysis.

GP130 binding to uPA will, after treatment with of PP-1 or PP-2 (or uPA or anti-β1-integrin antibody), suppress p53 and increase Stat3 activation and resistance to apoptosis.

Conclusions from Examples Regarding Mechanisms

The inventors' conception of mechanisms involved in lung epithelial injury, such as that mediated by bleo or relatively low concentrations of uPA (<5 nM) and their repair or prevention by the peptides of the present invention are depicted in the illustrations of FIGS. 16-19 and discussed in some detail in the Figure descriptions. The inventors do not wish to be bound by any mechanisms, but present and discuss such mechanisms here simply to provide a fuller understanding of their conception of why the compositions and methods of this invention have proven to be, or are expected to be, useful for treating acute lung injury and pulmonary fibrosis.

The references cited above and below are all incorporated by reference herein in their entirety, whether specifically incorporated or not. Having now fully described this invention, it will be appreciated by those skilled in the art that the same can be performed within a wide range of equivalent parameters, concentrations, and conditions without departing from the spirit and scope of the invention and without undue experimentation.

Documents Cited

1. Blasi F, Vassalli J D, and Dano K. Urokinase-type plasminogen activator: proenzyme, receptor, and inhibitors. *J Cell Biol* 104:801-804, 1987.
2. Shetty S and Idell S. Urokinase induces expression of its own receptor in Beas2B lung epithelial Cells. *J Biol Chem* 276:24549-24556, 2001.
3. Shetty S, Penduthiri U, Halady P K S, Azghani A and Idell S. Regulation of plasminogen activator expression by urokinase in lung epithelial cells. *Am J Physiol* (*Lung Cell Mol Physiol*) 283 :L319-L328, 2002.
4. Shetty S, Khalil B, Cines D B and Idell S. Regulation of plasminogen activator inhibitor expression by urokinase in lung epithelial cells. *J Biol Chem* 278:18124-18131,2003.
5. Shetty S, Gyetko M and Mazar A. Role of urokinase in p53 protein expression: participation in apoptosis and tumorigenesis. *J Biol Chem* 280(30):28133-41, 2005.
6. Chapman H A. Plasminogen activators, integrins, and the coordinated regulation of cell adhesion and migration. *Cur Opin Cell Biol* 9:714-724,1997.
7. Shetty S and Idell S. Urokinase/Urokinase Receptor-mediated Signaling in Cancer. Apoptosis, Cell Signaling and Human diseases: Mol Mechanisms. Vol. 2 Srivastava R. (Ed) Humana press Inc. Totowa N. J. PP: 167-177, 2006.
8. Shetty S, Padijnayayveetil J, Tucker T and Idell S. Regulation of Plasminogen Activation Pathways by the Lung Epithelium. *Am J Physiol Lung Cell Mol Physiol* (in press), 2007.
9. Shetty S, John J and Idell S. Fibrosis Including Fibrinolytic Pathways. Pleural Diseases. Eds Light, R & Lee G (in press), 2007.
10. Shetty S, Velusamy T, Shetty P K, Idell S, Mazar A P, Bhandary Y P and Shetty R S. Regulation of Urokinase Receptor Expression by p53: A Novel Role in Stabilization of uPAR mRNA. *Mol Cell Biol* 27:5607-5618,2007.
11. Shetty S, Shetty P K, Velusamy T, Bhandary Y P and Shetty R S. Induction of Plasminogen activator inhibitor-1 mRNA Stabilization by Tumor Suppressor Protein p53. *J Biol. Chem* (revised and resubmitted), 2007.
12. Shetty P, Velusamy T, Bhandary Y P, Liu M, Shetty R S and Shetty S. Posttranscriptional Regulation of Urokinase Expression by Tumor Suppressor Protein p53: A Novel Role in uPA mRNA Turnover. *Am J Resp Cell Mol Biol* (in press),2007.
13. Chapman H A, Allen C L and Stone O L. Abnormalities in pathways of fibrin turnover among patients with interstitial lung disease. *Am Rev Respir Dis* 133: 437-443,1986.
14. Idell S, James K K, Levin E G, Schwartz B S, Manchanda N, Maunder R J, Martin T R, McLarty J and Fair D S. Local abnormalities in coagulation and fibrinolytic pathways predispose to alveolar fibrin deposition in the adult respiratory distress syndrome. *J Clin Invest* 84:695-705,1989.
15. Idell S. Extravascular coagulation and fibrin deposition in acute lung injury. *New Horizons* 2:566-574,1994.
16. Chapman H A, Allen C L and Stone O L. Abnormalities in pathways of fibrin turnover among patients with interstitial lung disease. *Am Rev Respir Dis* 133: 437-443, 1986.
17. Chapman H A, Bertozzi P and Reilly J J. Role of enzymes mediating thrombosis and thrombolysis in lung disease. *Chest* 93: 1256-1263,1988.
18. Chapman H A. Disorders of lung matrix remodeling. *J Clin Invest.* 113:148-157, 2004.
19. Idell S. Coagulation, Fibrinolysis and Fibrin Deposition in Lung Injury and Repair. Phan S H and Thrall R S Pulmonary Fibrosis. 80, 743-776. NY, Marcel Dekker. Lung Biology in Health and Disease, 1995.
20. Horowitz J C, Rogers D S, Simon R H, Sisson T H and Thannickal V J. Plasminogen activation-induced pericellular fibronectin proteolysis promotes fibroblast apoptosis. *Am J Resp Cell Mol Biol* 38:78-87, 2007.
21. Hasday J D, Bachwich P R, Lynch J P III and Sitrin R G. Procoagulant and plasminogen activator activities of bronchoalveolar fluid in patients with pulmonary sarcoidosis. *Exp Lung Res* 14, 261 -278,1988.
22. Bertozzi P, Astedt B, Zenzius L, Lynch K, LeMaire F, Zapol W and Chapman H A Jr. Depressed bronchoalveolar urokinase activity in patients with adult respiratory distress syndrome. *New Eng J Med* 322:890-897, 1990.

23. Bachofen M and Weibel E R. Structural alterations of lung parenchyma in the adult respiratory distress syndrome. *Clin Chest Med* 3:35-56, 1982.
24. Barazzone C, Belin D, Piguet P-F, Vassalli J-D, and Sappino A-P. Plasminogen activator inhibitor-1 in acute hyperoxic mouse lung injury. *J Clin Invest* 98: 2666-2673, 996.
25. Olman M, Mackman N, Gladson C L, Moser K M and Loskutoff D J. Changes in procoagulant and fibrinolytic gene expression during bleomycin-induced lung injury in the mouse. *J Clin Invest* 96: 1621-1630, 1999.
26. Eitzman D T, McCoy R D, Zheng X, Fay W P, Ginsburg D and Simon R H. Bleomycin-induced pulmonary fibrosis in transgenic mice that either lack or overexpress the murine plasminogen activator inhibitor-1 gene. *J Clin Invest* 97: 232-237, 1996.
27. Sisson T H, Hattori N, Xu Y and Simon R H. Treatment of bleomycin-induced pulmonary fibrosis by transfer of urokinase-type plasminogen activator genes. *Human Gene Therapy*. 10(14):2315-23, 1999.
28. Jeffery P K. Remodeling in asthma and chronic obstructive diseases. *Am J Resp crit Care Med*. 164: S28-38,2001.
29. Tiddens H, Silverman M and Bush A. The role of inflammation in airway disease remodeling. *Am J Resp Crit care Med*. 162: S7-S10, 2000.
30. Shetty S, Velusamy T, Idell S, Tang H and Shetty P K. Regulation of Urokinase Receptor Expression by Protein Tyrosine Phosphatases. *Am J Physiol: Lung Cell Mol Physiol* 292:L414-L421, 2006.
31. Shetty S, Rao G N, Cines D B and Bdeir K. Urokinase induces activation of STAT3 in lung epithelial cells. *Am J Physiol: Lung Cell Mol Physiol* 291 :L772-780,2006.
32. Saksela O and Rifkin D B. Cell-associated plasminogen activation: regulation and physiological functions. *Ann Rev Cell Biol* 4:93-126, 1988.
33. Jo M, Thomas K S, Marozkina N, Amin T J, Silva C M, Parsons S J and Gonias S L. Dynamic assembly of the urokinase-type plasminogen activator signaling receptor complex determines the mitogenic activity of urokinase-type plasminogen activator. *J Biol Chem* 280(17):17449-57, 2005.
34. Mazzieri R and Blasi F. The urokinase receptor and the regulation of cell proliferation. *Thromb Haemost* 93(4): 641-6, 2005.
35. Mazar A P, Henkin J and Goldfarb R H. The urokinase plasminogen activator system in cancer: Implications for tumor angiogenesis and metastasis. *Angiogenesis* 3:15-32, 2000.
36. Shetty S, Kumar A, Johnson A, Pueblitz S and Idell S. Urokinase receptor in human malignant mesothelioma cells: role in tumor cell mitogenesis and proteolysis. *Am J Physiol* 268:L972-L982,1995.
37. Shetty S, Kumar A, Johnson A R and Idell S. Regulation of mesothelial cell mitogenesis by antisense oligonucleotides for the urokinase receptor. *Antisense Res Dev* 5:307-314,1995.
38. Shetty S, Kumar A, Johnson A R, Pueblitz S, Holiday D, Raghu G and Idell S. Differential expression of the urokinase receptor in fibroblasts from normal and fibrotic human lungs. *Am J Resp Cel Mol Biol*. 15:78-87,1996.
39. Shetty S and Idell S. Posttranscriptional regulation of urokinase receptor gene expression in lung carcinoma and malignant mesothelioma cells in vitro. *Mol Cell Biohem* 199:189-200, 1999.
40. Montuori N, Mattiello A, Mancini A, Taglialatela P, Caputi M, Rossi G and Ragno P. Urokinase-mediated posttranscriptional regulation of urokinase-receptor expression in non small cell lung carcinoma. *Int J Cancer* 105(3): 353-60, 2003
41. Li C, Zhang J, Jiang Y, Gurewich V, Chen Y and Liu J N. Urokinase-type plasminogen activator upregulates its own expression by endothelial cells and monocytes via the uPAR pathway. *Thromb Res* 103(3):221-32,2001.
42. Lau H K F and Ho J. Regulation of plasminogen activator inhibitor-1 secretion by urokinase and tissue plasminogen activators in rat epithelioid-type smooth muscle cells. *Br J Haematol* 117:151 -158, 2002.
43. Moore B B and Hogaboam C M. Animal models of human lung disease: Murine models of pulmonary fibrosis. *Am J Physiol Lung Cell Mol Physiol* 294:L152-L160, 2008.
44. Bishop A E. Pulmonary epithelial stem cells. *Cell Prolif* 37:89-96, 2004.
45. Adamson I Y, Young L and Bowden D H. Relationship of alveolar epithelial injury and repair to the induction of pulmonary fibrosis. *Am J Pathol* 130: 377-383, 1988.
46. Caiolfa V R, Zamai M, Malengo G, Andolfo A, Madsen C D, Sutin J, Digman M A, Gratton E, Blasi F and Sidenius N. Monomer dimer dynamics and distribution of GPI-anchored uPAR are determined by cell surface protein assemblies. *J Cell Biol* 179(5)1067-1082, 2007.
47. Vassalli J D, Sappino A P and Belin D. The plasminogen activator/plasmin system. *J Clin Invest* 88:1067-1072, 1991.
48. Idell S, Kumar A, Zwieb C, Holiday D, Koenig K B and Johnson A R. Effects of TGF-beta and TNF-alpha on procoagulant and fibrinolytic pathways of human tracheal epithelial cells. *Am J Physiol* 267:L693-L703,1994.
49. Gross T J, Simon R H, Kelly C J and Sitrin R G. Rat alveolar epithelial cells concomitantly express plasminogen activator inhibitor-1 and urokinase. *Am J Physiol* 260 :L286-L295,1991.
50. Gross T J, Simon R H and Sitrin R G. Expression of urokinase-type plasminogen activator by rat pulmonary alveolar epithelial cells. *Am J Resp Cell Mol Biol* 3:449-456, 1990.
51. Shetty S and Idell S. Posttranscriptional regulation of plasminogen activator inhibitor-1 in human lung carcinoma cells. *Am J Physiol* (Lung Cell Mol. Physiol) 278: L148-L156, 2000.
52. Ghiso J A A, Alonso D F, Farias E F, Gomez D E and Bal de Kier Joffe E. Deregulation of the signaling pathways controlling urokinase production. Its relationship with the invasive phenotype. *Eur J Biochem* 263: 295-304,1999.
53. Gyetko M R, Sitrin R G, Fuller J A, Todd R F, Petty H and Standiford T J. Function of the urokinase receptor (CD87) in neutrophil chemotaxis. *J Leu Biol* 58:533-538, 1995. Gyetko M R, Todd R F, Wilkinson C C and Sitrin R G. The urokinase receptor is required for human monocyte chemotaxis in vitro. *J Clin Invest* 93:1380-1387, 1994.
54. Sprengers E D and Kluft C. Plasminogen activator inhibitors. *Blood* 69, 381-387, 1987.
55. Loskutoff D J, Sawdey M and Mimuro J. Type 1 plasminogen activator inhibitor. *Prog Hemost Thromb* 9:87-115, 1989.
56. Barchowsky A, Roussel R R, Kreiser R J, Mossman B T and Treadwell M D. Expression and activity of urokinase and its receptor in endothelial and pulmonary epithelial cells exposed to asbestos. *Toxicol Appl Pharmacol* 152, 388-396,1998.
57. Lardot C G, Huaux F A, Broeckaert F R, Declerck P J, Delos M, Fubini B and Lison D F. Role of urokinase in the fibrogenic response of the lung to mineral particles. *Am J Resp Crit Care Med* 157:617-628,1998.

58. Falcone D J, McCaffrey T A, Mathew J, McAdam K and Borth W. THP-1 macrophage membrane-bound plasmin activity is up-regulated by transforming growth factor-beta 1 via increased expression of urokinase and the urokinase receptor. *J Cell Physiol* 164:334-343,1995.
59. Dang C V, Bell W R, Kaiser D and Wong A. Disorganization of cultured vascular endothelial cell monolayers by fibrinogen fragment D. *Science* 227:1487-1490,1985.
60. Davis D W, Weidner D A, Holian A and McConkey D J. Nitric oxide-dependent activation of p53 suppresses bleomycin-induced apoptosis in the lung. *J Exp Med* 192(6): 857-69, 2000.
61. Nishiuma T, Sisson T H, Subbotina N and Simon R H. Localization of plasminogen activator activity within normal and injured lungs by in situ zymography. *Am J Resp Cell Mol Biol* 31(5):552-8, 2004.
62. Swaisgood C M, French E L, Noga C, Simon R H and Ploplis V A. The development of bleomycin-induced pulmonary fibrosis in mice deficient for components of the fibrinolytic system. *Am J Pathol* 157(1):177-87, 2000.
63. Hattori N, Mizuno S, Yoshida Y, Chin K, Mishima M, Sisson T H, Simon R H, Nakamura T and Miyake M. The plasminogen activation system reduces fibrosis in the lung by a hepatocyte growth factor-dependent mechanism. *Am J Pathol* 164(3):1091-8, 2004.
64. Plataki M, Koutsopoulos A V, Darivianaki K, Delides G, Siafakas N M and Bouros D. Expression of apoptotic and antiapoptotic markers in epithelial cells in idiopathic pulmonary fibrosis. *Chest* 127(1):266-74, 2005.
65. Hall p, Mckee P, Menage H, Dover R and Lane D. High levels of p53 protein in UV-irradiated normal human skin. *Oncogene* 8:203-207, 1993.
66. Mishra A, Liu J Y, Brody A R and Morris G F. Inhaled asbestos fibers induce p53 expression in the rat lung. *Am J Resp Cell Mol Biol* 16(4):479-85, 1997.
67. Xu J and Morris G F. p53-mediated regulation of proliferating cell nuclear antigen expression in cells exposed to ionizing radiation. *Mol Cell Biol* 19(1):12-20, 1999.
68. Mishra A, Doyle N A and Martin W J. Bleomycin-mediated pulmonary toxicity: evidence for a p53-mediated response. *Am J Resp Cell Mol Biol* 22(5):543-549, 2000.
69. Wygrecka M, Markart P, Ruppert C, Petri K, Preissner K T, Seeger W and Guenther A. Cellular origin of pro-coagulant and (anti)-fibrinolytic factors in bleomycin-injured lungs. *Eur Resp J* 29(6):1105-1114 2007.
70. Schelegle E S, Mansoor J K and Giri S. Pirfenidone attenuates bleomycin-induced changes in pulmonary functions in hamsters. *Pro Soc Exp Biol Med* 216(3):392-397, 1997.
71. Allio T and Preston R J. Increased sensitivity to chromatid aberration induction by bleomycin and neocarzinostatin results from alterations in a DNA damage response pathway. *Mutation Res* 453(1):5-15,2000.
72. Okudela K, Ito T, Mitsui H, Hayashi H, Udaka N, Kanisawa M and Kitamura H. The role of p53 in bleomycin-induced DNA damage in the lung. A comparative study with the small intestine. *Am J Pathol* 155(4):1341-51,1999.
73. Ozawa S, Suzuki H, Nishimura T and Tanaka N. Cellular uptake and efflux of peplomycin in sensitive and bleomycin-resistant subline of mouse lymphoblastoma L5178Y cells. *J Antibiotics* 41(3):395-397,1988.
74. Ghosh S, Mendoza T, Ortiz L A, Hoyle G W, Fermin C D, Brody A R, Friedman M and Morris G F. Bleomycin sensitivity of mice expressing dominant-negative p53 in the lung epithelium. *Am J Resp Crit Care Med* 166(6):890-7, 2002.
75. Alfano D, Franco P, Vocca I, Gambi N, Pisa V, Mancini A, Caputi M, Carriero M V, Iaccarino I and Stoppelli M. The urokinase plasminogen activator and its receptor; Role in cell growth and apoptosis. *Throm Haemost* 93:205-211, 2005.
76. Lardot C G, Huaux F A, Broeckaert F R, Declerck P J, Delos M, Fubini B and Lison D F. Role of urokinase in the fibrogenic response of the lung to mineral particles. *Am J Resp Crit Care Med* 157(2):617-28, 1998.
77. Wei Y, Lukashev M E, Simon D I, Bodary S C, Rosenberg S, Doyle M V and Chapman H A. Regulation of integrin function by the urokinase receptor. *Science* 273:1551-1555, 1996.
78. Zhang F, Tom C C, Kugler M C, Ching T T, Kreidberg J A, Wei Y and Chapman H A. Distinct ligand binding sites in integrin a3b1 regulate matrix adhesion and cell-cell contact. *J Cell Biol* 163: 177-188, 2003.
79. Wei Y, Czekay R, Robillard L, Kugler M C, Zhang F, Kim K K, Xiong J P, Humphries M J and Chapman H A. Regulation of a5b1 integrin conformation and function by urokinase receptor binding. *J Cell Biol* 168:501-511, 2005.
80. Carlin S M, Resink T J, Tamm M and Roth M. Urokinase signal transduction and its role in cell migration. *FASEB J* 19: 195-202, 2005.
81. Idell S, James K K and Coalson J J. Fibrinolytic activity in bronchoalveolar lavage of baboons with diffuse alveolar damage: trends in two forms of lung injury. *Crit Care Med* 20(10): 1431-40, 1992.
82. Idell S, Peterson B T, Gonzalez K K, Gray L D, Bach R, McLarty J and Fair D S. Local abnormalities of coagulation and fibrinolysis and alveolar fibrin deposition in sheep with oleic acid-induced lung injury. *Am Rev Resp Dis* 138 (5):1282-94, 1988.
83. Idell S, Gonzalez K K, MacArthur C K, Gillies C, Walsh P N, McLarty J and Thrall R S. Bronchoalveolar lavage procoagulant activity in bleomycin-induced lung injury in marmosets. Characterization and relationship to fibrin deposition and fibrosis. *Am Rev Resp Dis* 136(1): 124-33, 1987.
84. Idell S, Thrall R S, Maunder R, Martin T R, McLarty J, Scott M and Starcher B C. Bronchoalveolar lavage desmosine in bleomycin-induced lung injury in marmosets and patients with adult respiratory distress syndrome. *Exptl Lung Res* 15(5):739-53, 1989.
85. Idell S, James K K, Gillies C, Fair D S and Thrall R S. Abnormalities of pathways of fibrin turnover in lung lavage of rats with oleic acid and bleomycin-induced lung injury support alveolar fibrin deposition. *Am J Pathol* 135(2):387-99, 1989.
86. Coalson J J, Winter V T, Gerstmann D R, Idell S, King R J and Delemos R A. Pathophysiologic, morphometric, and biochemical studies of the premature baboon with bronchopulmonary dysplasia. *Am Rev Resp Dis* 145(4 Pt 1):872-81, April 1992.
87. Idell S, Koenig K B, Fair D S, Martin T R, McLarty J and Maunder R J. Serial abnormalities of fibrin turnover in evolving adult respiratory distress syndrome. *Am J Physiol* 261(4 Pt 1):L240-8, 1991.
88. Abraham E, Gyetko M R, Kuhn K, Arcaroli J, Strassheim D, Park J S, Shetty S and Idell S. Urokinase-type plasminogen activator potentiates lipopolysaccharide-induced neutrophil activation. *J Immunol* 170(11):5644-51, 2003.
89. Sturge J, Hamelin J and Jones G E. N-WASP activation by a □1-integrin-dependent mechanism supports PI3K-independent chemotaxis stimulated by urokinase-type plasminogen activator. *J Cell Sci* 115:699-711.

90. Mazzieri R, D'Alessio S, Kenmoe R K, Ossowski L and Blasi F. An uncleavable uPAR mutant allows dissection of signaling pathways in uPA-dependent cell migration. *Mol Biol Cell* 17:367-378, 2006.

91. Liang O D, Chavakis T, Linder M, Bdeir K, Kuo A and Preissner K T. Binding of urokinase plasminogen activator to gp130 via a putative urokinase-binding consensus sequence. *Biol Chem* 384:229-236, 2003.

92. Shushakova N, Tkachuk N, Danger M, Tkachuk S, Park J K, Zwimer J, Hashimoto K, Haller H and Dulmer I. Urokinase-induced activation of the gp130/tyk2/Stat3 pathway mediates a pro-inflammatory effect in human mesengial cells va expression of the anaphylatoxin C5a receptor. *J Cell Sci* 118: 2743-2753, 2005.

93. Cao D, Tal T L, Graves L M, Gilmour I, Linak W, Reed W, Bromberg P A and Samet J M. Diesel exhaust particulate-induced activation of Stat3 requires activities of EGFR and Src in airway epithelial cells. *Am J Physiol Lung Cell Mol Physiol* 292:L422-L429, 2007.

94. Gunther A, Lubke N, Ermert M, Schermuly R T, Weissmann N, Breithecker A, Markrt P, Ruppert C, Quanz K, Ermert L, Grimminger F and Seeger W. Prevention of bleomycin-induced lung fibrosis by aerosolization of heparin or urokinase in rabbits. *Am J Respir Crit Care Med* 168:1358-1365, 2003.

95. Mollar A S, Nachar M, Jordi G G, Closa D, Xaubet A and Bulbena O. Intratracheal transplantation of alveolar type II cells reverses bleomycin-induced lung fibrosis. *Am J Resp Crit Care Med* 176: 1261-68, 2007.

96. Starcher B C. Lung elastin and matrix. *Chest* 117(5 Suppl 1):229S-34S, 2000.

97. Starcher B and Kuhn C. Combining histology and biochemical measurements of connective tissue components in small samples of lung: application to bleomycin-induced fibrosis in the mouse. *Exptl Lung Res* 29:179-194, 2003.

98. Viscardi R M, Broderick K, Sun C C, Yale-Loehr A J, Hessamfar A, Taciak V, Burke K C, Koenig K B and Idell S. Disordered pathways of fibrin turnover in lung lavage of premature infants with respiratory distress syndrome. *Am Rev Resp Dis* 146(2):492-9, 1992.

99. Idell S, Mazar A, Cines D, Kuo A, Parry G, Gawlak S, Juarez J, Koenig K, Azghani A, Hadden W, McLarty J and Miller E. Single-chain urokinase alone or complexed to its receptor in tetracycline-induced pleuritis in rabbits. *Am J Resp Crit Care Med* 166(7):920-6, 2002.

100. Shetty S, Muniappa H B, Halady P K S and Idell S. Regulation of Urokinase Receptor Expression by Phosphoglycerate Kinase. *Am J Resp Cell Mol Biol* 31:100-106, 2004.

101. Shetty S, Ganachary M, Liu M, Azghani A, Muniyappa H and Idell S. Regulation of urokinase receptor expression by phosphoglycerate kinase is independent of its catalytic activity. *Am J Physiol* 289(4):L591-8, 2005.

102. Shetty S. Regulation of Urokinase Receptor mRNA Stability by hnRNPC in Lung Epithelial Cells. *Mol Cell Bio* 272:107-118, 2005.

103. Shetty S, Kumar A and Idell S. Posttranscriptional regulation of urokinase receptor mRNA: identification of a novel urokinase receptor mRNA binding protein in human mesothelioma cells. *Mol Cell Biol* 17:1075-1083, 1997.

104. Wei Y, Yang X, Liu Q, Wilkins J A and Chapman H A. A role of caveolin and the urokinase receptor in integrin-mediated adhesion and signaling. *J Cell Biol* 144:1285-1294, 1999.

105. Wanaski S P, Ng B K and Glaser M. Caveolin scaffolding region and the membrane binding region of Src form lateral membrane domains. *Biochem* 42:42-56, 2003.

106. Hogg N and Porter J C. Integrins take partners: cross-talk between integrins and other membrane receptors. *Trends in Cell Biology* 8:390-396, 1998.

107. Armulik A, Velling T and Johansson S. The integrin □1 subunit transmembrane domain regulates phosphotidylinositol 3-kinase-dependent tyrosine phosphorylation of Crk-associated substrate. *Mol Biol Cell* 15:2558-2567, 2004.

108. Velling T, Nilsson S, Stefansson A and Johansson S. □1 -integrins induce phosphorylation of Akt on serine 473 independently of focal adhesion kinase and src family kinases. *EMBO* 5:901-905, 2004.

109. Tian B, Lessan K, Kahm J, Kleidon J and Henke C. beta 1 integrin regulates fibroblast viability during collagen matrix contraction through a phosphatidylinositol 3-kinase/Akt/protein kinase B signaling pathway. *J Biol Chem* 277(27):24667-75, 2002.

110. Xia H, Nho R S, Kahm J, Kleidon J and Hanke C A. Focal adhesion kinase is upstream of phosphotidylinositol 3-kinase/Akt in regulating fibroblast survival in response to contraction of type I collagen matrices via a b1 integrin viability signaling pathway. *J Biol Chem* 279(31):33024-34,2004.

111. Nho R S, Xia H, Kahm J, Kleidon J, Diebold D and Henke C A. Role of integrin-linked kinase in regulating phosphorylation of Akt and fibroblast survival in Type I Collagen matrices through a b1 integrin viability signaling pathway. *J Biol Chem* 280 (28):26630-39, 2005.

112. Benson E M and Longo P J M. Urokinase-type plasminogen activator receptor regulates a novel pathway of fibronectin matrix assembly requiring Src-dependent transcativation of epidermal growth factor receptor. *J Biol Chem* 281(14) 9450-9459, 2006.

113. Guerrero J, Santibanez J F, Gonzalez A and Martinez J. EGF receptor transcativation by urokinase receptor stimulus through a mechanism involving Src and matrix matelloproteinases. *Exptl Cell Res* 292 (1) 201-208, 2004.

114. Sethanandam G, Smith G T, Fields J R, Fornwald L W and Anderson L M. Alternate paths from epidermal growth factor receptor to Akt in malignant transformed lung epithelial cells. *Am J Resp Cell Mol Biol* 33: 490-499, 2005.

115. Liu D, Ghiso J A A, Estrada Y and Ossowsi L. EGFR is a transducer of the urokinase receptor initiated signal that is required for in vivo growth of a human carcinoma. *Cancer Cell* 1: 445-457, 2002.

116. Wei Y, Eble J A, Wang Z, Kreidberg J A and Chapman H A. Urokinase receptors promote □1 integrin function through interaction with integrin a3b1. *Mol Biol Cell Biol* 12:2975-2986, 2001.

117. Shetty P, Velusamy T, Liu M, Bhanday Y P and Shetty S. Urokinase-mediated Tyrosine Phosphorylation of Phosphoglycerate kinase regulates Urokinase receptor expression. *J Biol Chem (revised and resubmitted)* 2008.

118. Velusamy T, Shetty P K, Liu M, Bhanday Y P and Shetty S. Regulation of Urokinase Receptor Expression by hnRNPC. *Biochem (revised and resubmitted)* 2008.

119. Lin J, Tang H, Jin X, Jia G and Hsieh J. p53 regulates Stat3 phosphorylation and DNA binding activity in human prostate cancer cells expressing constitutively active Stat3. *Oncogene* 21:3082-3088, 2002.

120. Lin J, Jin X, Rothman K, Lin H, Tang H and Burke W. Modulation of signal transducer and activator of transcription 3 activities by p53 tumor suppressor in breast cancer cells. *Cancer Res* 62: 376-380, 2002.

121. Niu G, Wright K L, Ma Y, Wright G M, Huang M, Irby R, Briggs J, Karras J, Cress W D, Pardoll D, Jove R, Chen J and Yu H. Role of Stat3 in regulating p53 expression and functions. *Mol Cell Biol* 25(17) 7432-7440, 2005.
122. Kortlever R M, Higgins P J and Bernards R. Plasminogen activator inhibitor-1 is critical downstream target of p53 in the induction of replicative senescence. *Nature Cell Biol* 8:877-884, 2006.
123. Wunderlich S, Gruh I, Winkler M E, Beier J, Radtke K, Schmiedl A, Groos S, Haverich A, Martin U. Type II Pneumocyte-Restricted Green Fluorescent Protein Expression After Lentiviral Transduction of Lung Epithelial Cells. *Hum Gene Ther (in press)* 2007.
124. Gruh I, Wunderlich S, Winkler M, Schwanke K, Heinke J, Blömer U, Ruhparwar A, Rohde B, Li R K, Haverich A, Martin U. Human CMV immediate-early enhancer: a useful tool to enhance cell-type-specific expression from lentiviral vectors. *J Gene Med* 10(1):21-32, 2008.
125. Epperly m W, Bray J A, Krager S, Berry L M, Gooding W, Engelhardt J F, Zwacka R, Travis E L and Greenberger J S. Intratracheal injection of adenovirus containing the human MnSOD trangene protects athymic nude mice from irradiation-induced organizing alveolitis. *Int J Radiat Oncol Biol Phys* 43: 169-181, 1999.

What is claimed is:

1. A method for treating acute lung injury or pulmonary fibrosis that is associated with apoptosis of lung epithelium in a subject, comprising administering to the subject suffering from said acute lung injury or pulmonary fibrosis an effective amount of the following anti-apoptotic or anti-fibrotic compound or composition:
   (a) a peptide PP-1 the sequence of which is DGIWKAS-FTTFTVTKYWFYR (SEQ ID NO:1), or
   (b) a fragment of PP-1, with the proviso that the fragment is not Tyr-Arg or Ile-Trp, or
   (c) a pharmaceutical composition comprising said peptide or said fragment and a pharmaceutically acceptable carrier.

2. A method for treating acute lung injury or pulmonary fibrosis that is associated with apoptosis of lung epithelium in a subject, comprising administering to the subject suffering from said acute lung injury or pulmonary fibrosis an effective amount of the following anti-apoptotic or anti-fibrotic compound or composition:
   (a) a peptide multimer comprising peptide PP-1 (SEQ ID NO:1) which multimer has the formula $(P^1-Gly_z)_n-P^2$, wherein:
   each of $P^1$ and $P^2$ is PP-1,
   z=0-6; and
   n=1-25;
      wherein the peptide multimer has at least 20% of the biological activity of peptide PP-1 in an in vitro or in vivo assay, or
   (b) a pharmaceutical composition comprising said peptide multimer and a pharmaceutically acceptable carrier.

3. The method of claim 1, wherein the pharmaceutical composition is in
   (a) a form suitable for injection; or
   (b) a form suitable for instillation into lungs.

4. A method for treating acute lung injury or pulmonary fibrosis that is associated with apoptosis of lung epithelium in a subject, comprising administering to the subject suffering from said acute lung injury or pulmonary fibrosis an effective amount of a peptide of SEQ ID NO: 1 or fragment thereof with the proviso that the fragment is not Tyr-Arg or Ile-Trp, which peptide or fragment is non-covalently bound to or associated with a cell-targeting delivery or translocation molecule or moiety.

5. The method of claim 1, wherein said subject is a human.

6. The method of claim 3, wherein said subject is a human.

7. The method of claim 1, wherein said fragment of PP-1 (SEQ ID NO:1), or said pharmaceutical composition comprising said fragment, is administered to said subject.

8. The method of claim 7, wherein said subject is a human.

9. A method for treating acute lung injury or pulmonary fibrosis that is associated with apoptosis of lung epithelium in a subject, comprising administering to the subject suffering from said acute lung injury or pulmonary fibrosis an effective amount of
   (a) a peptide multimer comprising peptide PP-1 (SEQ ID NO:1) which multimer has the formula $(P^1-Gly_z)_n-P^2$, wherein:
   each of $P^1$ and $P^2$ is PP-1;
   z=0-6; and
   n=1-25;
      which peptide multimer has at least 20% of the biological activity of peptide PP-1 in an in vitro or in vivo assay,
      wherein the peptide multimer is non-covalently bound to, or associated with, a cell-targeting delivery or translocation molecule or moiety, or
   (b) a pharmaceutical composition comprising (a) and a pharmaceutically acceptable carrier.

10. A method for treating acute lung injury or pulmonary fibrosis that is associated with apoptosis of lung epithelium in a subject, comprising administering to the subject suffering from said acute lung injury or pulmonary fibrosis an effective amount of the following anti-apoptotic or anti-fibrotic compound or composition:

(a) a peptide multimer comprising peptide PP-1, SEQ ID NO:1, which multimer:
  (i) has the formula $P^1_n$ wherein
     $P^1$ is PP-1, and
     n=2-5, or
  (ii) has the formula $(P^1-X_m)_n-P^2$, wherein
     each of $P^1$ and $P^2$ is PP-1;
     X is $C_1-C_5$ alkylene, $C_1-C_5$ alkenylene, $C_1-C_5$ alkynylene, or $C_1-C_5$ polyether containing up to 4 oxygen atoms;
     m=0 or 1; and
     n=1-7, and
  wherein the peptide multimer has at least 20% of the biological activity of peptide PP-1 in an in vitro or in vivo assay; or
(b) a pharmaceutical composition comprising said peptide multimer and a pharmaceutically acceptable carrier.

11. A method for treating acute lung injury or pulmonary fibrosis that is associated with apoptosis of lung epithelium in a subject, comprising administering to the subject suffering from said acute lung injury or pulmonary fibrosis an effective amount of a peptide multimer comprising peptide PP-1 (SEQ ID NO:1) which multimer:
  (i) has the formula $P^1_n$ wherein
     $P^1$ is PP-1 (SEQ ID NO:1), and
     n=2-5, or
  (ii) has the formula $(P^1-X_m)_n-P^2$, wherein
     each of $P^1$ and $P^2$ is PP-1 (SEQ ID NO:1);
     X is $C_1-C_5$ alkylene, $C_1-C_5$ alkenylene, $C_1-C_5$ alkynylene, $C_1-C_5$ polyether containing up to 4 oxygen atoms;
     m=0 or 1; and
     n=1-7,
     which multimer of (i) and (ii) has at least 20% of the biological activity of peptide PP-1 in an in vitro or in vivo assay;
  wherein the peptide multimer of (i) and (ii) is non-covalently bound to, or associated with, a cell-targeting delivery or translocation molecule or moiety, or
  (iii) a pharmaceutical composition comprising (i) or (ii) and a pharmaceutically acceptable carrier.

12. A method for treating acute lung injury or pulmonary fibrosis that is associated with apoptosis of lung epithelium in a subject, comprising administering to the subject suffering from said acute lung injury or pulmonary fibrosis an effective amount of:
  (i) a fusion polypeptide comprising a peptide multimer comprising peptide PP-1 (SEQ ID NO:1) which multimer has the formula $(P^1-Gly_z)_n-P^2$, wherein
     each of $P^1$ and $P^2$ is PP-1,
     z=0-6; and
     n=1-25;
     which peptide multimer has at least 20% of the biological activity of peptide PP-1 in an in vitro or in vivo assay,
     fused to a delivery or translocation protein or peptide that is selected from the group consisting of:
     (a) HIV-TAT protein;
     (b) penetratin the sequence of which is RQIKIWFQNRRMKWKK (SEQ ID NO:6);
     (c) a penetratin variant W48F the sequence of which is RQIKIFFQNRRMKWKK (SEQ ID NO:7);
     (d) a penetratin variant W56F the sequence of which is RQIKIWFQNRRMKFKK, SEQ ID NO:8);
     (e) a penetratin variant the sequence of which is RQIKIWFQNRRMKFKK, SEQ ID NO:9);
     (f) herpes simplex virus protein VP22;
     (g) Marek's disease virus protein UL49; and
     (h) DelPep-1, the sequence of which is KETWWETWWTEWSQPKKKRKV (SEQ ID NO:10), or
  (ii) an admixture of said peptide multimer with any of (a)-(h), or
  (iii) a pharmaceutical composition comprising (i) or (ii) and a pharmaceutically acceptable carrier.

13. A method for treating acute lung injury or pulmonary fibrosis that is associated with apoptosis of lung epithelium in a subject, comprising administering to the subject suffering from said acute lung injury or pulmonary fibrosis an effective amount of:
  (i) a fusion polypeptide comprising a peptide PP-1 (SEQ ID NO:1) fused to a delivery or translocation protein or peptide selected from the group consisting of:
     (a) HIV-TAT protein;
     (b) penetratin the sequence of which is RQIKIWFQNRRMKWKK (SEQ ID NO:6);
     (c) a penetratin variant W48F the sequence of which is RQIKIFFQNRRMKWKK (SEQ ID NO:7);
     (d) a penetratin variant W56F the sequence of which is RQIKIWFQNRRMKFKK, SEQ ID NO:8);
     (e) a penetratin variant the sequence of which is RQIKIWFQNRRMKFKK, SEQ ID NO:9);
     (f) herpes simplex virus protein VP22;
     (g) Marek's disease virus protein UL49; and
     (h) DelPep-1, the sequence of which is KETWWETWWTEWSQPKKKRKV (SEQ ID NO:10), or
  (ii) an admixture of peptide PP-1 (SEQ ID NO:1) or a fragment of PP-1 with any of (a)-(h), with the proviso that the fragment is not Tyr-Arg or Ile-Trp, or
  (iii) a pharmaceutical composition comprising (i) or (ii) and a pharmaceutically acceptable carrier.

14. A method for treating acute lung injury or pulmonary fibrosis that is associated with apoptosis of lung epithelium in a subject, comprising administering to the subject suffering from said acute lung injury or pulmonary fibrosis an effective amount of:
  a fusion polypeptide comprising a peptide multimer comprising peptide PP-1 (SEQ ID NO:1) which multimer
    (A) has the formula $P^1_n$ wherein
       $P^1$ is PP-1, and
       n=2-5, or
    (B) has the formula $(P^1-X_m)_n-P^2$, wherein
       each of $P^1$ and $P^2$ is PP-1;
       X is $C_1-C_5$ alkylene, $C_1-C_5$ alkenylene, $C_1-C_5$ alkynylene, or $C_1-C_5$ polyether containing up to 4 oxygen atoms;
       m=0 or 1; and
       n=1-7,
       which multimer has at least 20% of the biological activity of peptide PP-1 in an in vitro or in vivo assay and
       which multimer is fused to a delivery or translocation protein or polypeptide selected from the group consisting of:
       (a) HIV-TAT protein;
       (b) penetratin the sequence of which is RQIKIWFQNRRMKWKK (SEQ ID NO:6);
       (c) a penetratin variant W48F the sequence of which is RQIKIFFQNRRMKWKK (SEQ ID NO:7);
       (d) a penetratin variant W56F the sequence of which is RQIKIWFQNRRMKFKK, SEQ ID NO:8);
       (e) a penetratin variant the sequence of which is RQIKIWFQNRRMKFKK, SEQ ID NO:9);
       (f) herpes simplex virus protein VP22;
       (g) Marek's disease virus protein UL49; and (h) DelPep-1, the sequence of which is KETWWETW-WTEWSQPKKKRKV (SEQ ID NO:10), or
(ii) an admixture of the peptide multimer of (i)(A) or (i)(B) with any of (a)-(h), or
(iii) a pharmaceutical composition comprising (i) or (ii) and a pharmaceutically acceptable carrier.

\* \* \* \* \*

SEQUENCE LISTING

<160> NUMBER OF SEQ ID NOS: 10

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Asp Gly Ile Trp Lys Ala Ser Phe Thr Thr Phe Thr Val Thr Lys Tyr
1               5                   10                  15

Trp Phe Tyr Arg
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Trp Gly Ile Asp Lys Ala Phe Phe Thr Thr Ser Thr Val Thr Tyr Lys
1               5                   10                  15

Trp Phe Arg Tyr
            20

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Asn Tyr His Tyr Leu Glu Ser Ser Met Thr Ala Leu Tyr Thr Leu Gly
1               5                   10                  15

His

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Ala Glu Ser Thr Tyr His His Leu Ser Leu Gly Tyr Met Tyr Thr Leu
1               5                   10                  15

Asn

<210> SEQ ID NO 5
<211> LENGTH: 178
<212> TYPE: PRT
<213> ORGANISM: human Caveolin-1

<400> SEQUENCE: 5

```
Met Ser Gly Gly Lys Tyr Val Asp Ser Glu Gly His Leu Tyr Thr Val
  1               5                  10                  15

Pro Ile Arg Glu Gln Gly Asn Ile Tyr Lys Pro Asn Asn Lys Ala Met
             20                  25                  30

Ala Asp Glu Leu Ser Glu Lys Gln Val Tyr Asp Ala His Thr Lys Glu
         35                  40                  45

Ile Asp Leu Val Asn Arg Asp Pro Lys His Leu Asn Asp Asp Val Val
 50                  55                  60

Lys Ile Asp Phe Glu Asp Val Ile Ala Glu Pro Gly Thr His Ser
 65                  70                  75                  80

Phe Asp Gly Ile Trp Lys Ala Ser Phe Thr Thr Phe Thr Val Thr Lys
                 85                  90                  95

Tyr Trp Phe Tyr Arg Leu Leu Ser Ala Leu Phe Gly Ile Pro Met Ala
                100                 105                 110

Leu Ile Trp Gly Ile Tyr Phe Ala Ile Leu Ser Phe Leu His Ile Trp
            115                 120                 125

Ala Val Val Pro Cys Ile Lys Ser Phe Leu Ile Glu Ile Gln Cys Ile
        130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile
```

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

```
Arg Gln Ile Lys Ile Trp Phe Gln Asn Arg Arg Met Lys Trp Lys Lys
  1               5                  10                  15
```

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

```
Arg Gln Ile Lys Ile Phe Phe Gln Asn Arg Arg Met Lys Trp Lys Lys
  1               5                  10                  15
```

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

```
Arg Gln Ile Lys Ile Trp Phe Gln Asn Arg Arg Met Lys Phe Lys Lys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Arg Gln Ile Lys Ile Phe Phe Gln Asn Arg Arg Met Lys Phe Lys Lys
1               5                   10                  15

<210> SEQ ID NO 10
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Lys Glu Thr Trp Trp Glu Thr Trp Trp Thr Glu Trp Ser Gln Pro Lys
1               5                   10                  15

Lys Lys Arg Lys Val
            20
```